(12) United States Patent
Crichton et al.

(10) Patent No.: US 11,653,939 B2
(45) Date of Patent: May 23, 2023

(54) MICROPROJECTION ARRAYS WITH MICROPROJECTIONS HAVING LARGE SURFACE AREA PROFILES

(71) Applicant: Vaxxas Pty Limited, Sydney (AU)

(72) Inventors: Michael Crichton, Auchenflower (AU); Mark Anthony Fernance Kendall, Chelmer (AU)

(73) Assignee: VAXXAS PTY LIMITED, Sydney (AU)

( * ) Notice: Subject to any disclaimer, the term of this patent is extended or adjusted under 35 U.S.C. 154(b) by 101 days.

(21) Appl. No.: 17/393,096

(22) Filed: Aug. 3, 2021

(65) Prior Publication Data

US 2022/0015782 A1      Jan. 20, 2022

Related U.S. Application Data

(63) Continuation of application No. 15/760,869, filed as application No. PCT/AU2016/050867 on Sep. 16, 2016, now Pat. No. 11,103,259.

(Continued)

(51) Int. Cl.
*A61B 17/20* (2006.01)
*A61M 37/00* (2006.01)

(52) U.S. Cl.
CPC ....... *A61B 17/205* (2013.01); *A61M 37/0015* (2013.01); *A61M 2037/0046* (2013.01); *A61M 2037/0061* (2013.01)

(58) Field of Classification Search
CPC ...... A61M 2037/0046; A61M 37/0015; A61M 2037/0023; A61M 2037/003; A61M 2037/0038; A61M 2037/0053; A61M 2037/0061; A61M 5/3134; A61M 5/32; A61M 2005/3201; A61M 2005/3212; A61M 5/3286; A61M 5/329; A61K 9/0021

See application file for complete search history.

(56) References Cited

U.S. PATENT DOCUMENTS 2,213,830 A    9/1940   Anastasi
2,881,500 A    4/1959   Furness
(Continued)

FOREIGN PATENT DOCUMENTS

CN    1149018 A    5/1997
CN    101214395 A    7/2008
(Continued)

OTHER PUBLICATIONS

U.S. Appl. No. 14/351,499, filed Apr. 11, 2014, Delivery Device.
(Continued)

*Primary Examiner* — Bhisma Mehta
*Assistant Examiner* — William R Frehe
(74) *Attorney, Agent, or Firm* — Seed IP Law Group LLP

(57) ABSTRACT

A microprojection array comprising a substrate with a plurality of microprojections protruding from the substrate wherein the microprojections have a tapering hexagonal shape and comprise a tip and a base wherein the base has two substantially parallel sides with a slight draught angle of approximately 1 to 20 degrees up to a transition point at which point the angle increases to from about 20 degrees to about 70 degrees.

9 Claims, 6 Drawing Sheets

Related U.S. Application Data

(60) Provisional application No. 62/220,308, filed on Sep. 18, 2015.

(56) References Cited

U.S. PATENT DOCUMENTS

| | | |
|---|---|---|
| 4,702,799 A | 10/1987 | Tuot |
| 5,017,007 A | 5/1991 | Milne et al. |
| 5,201,992 A | 4/1993 | Marcus et al. |
| 5,353,792 A | 10/1994 | Lübbers et al. |
| 5,449,064 A | 9/1995 | Hogan et al. |
| 5,457,041 A | 10/1995 | Ginaven et al. |
| 5,461,482 A | 10/1995 | Wilson et al. |
| 5,499,474 A | 3/1996 | Knooihuizen |
| 5,527,288 A | 6/1996 | Gross et al. |
| 5,611,806 A | 3/1997 | Jang |
| 5,657,138 A | 8/1997 | Lewis et al. |
| 5,859,937 A | 1/1999 | Nomura |
| 5,870,806 A | 2/1999 | Black, Jr. |
| 5,922,356 A | 7/1999 | Koseki et al. |
| 5,928,207 A | 7/1999 | Pisano et al. |
| 5,943,075 A | 8/1999 | Lee et al. |
| 6,052,652 A | 4/2000 | Lee |
| 6,233,797 B1 | 5/2001 | Neely et al. |
| 6,287,556 B1 | 9/2001 | Portnoy et al. |
| 6,299,621 B1 | 10/2001 | Fogarty et al. |
| 6,334,856 B1 | 1/2002 | Allen et al. |
| 6,352,697 B1 | 3/2002 | Cox et al. |
| 6,454,755 B1 | 9/2002 | Godshall |
| 6,463,312 B1 | 10/2002 | Bergveld et al. |
| 6,478,738 B1 | 11/2002 | Hirabayashi et al. |
| 6,503,231 B1 | 1/2003 | Prausnitz et al. |
| 6,533,949 B1 | 3/2003 | Yeshurun et al. |
| 6,537,242 B1 | 3/2003 | Palmer |
| 6,537,264 B1 | 3/2003 | Cormier et al. |
| 6,551,849 B1 | 4/2003 | Kenney |
| 6,557,849 B2 | 5/2003 | Wyss |
| 6,558,361 B1 | 5/2003 | Yeshurun |
| 6,565,532 B1 | 5/2003 | Yuzhakov et al. |
| 6,589,202 B1 | 7/2003 | Powell |
| 6,591,124 B2 | 7/2003 | Sherman et al. |
| 6,610,382 B1 | 8/2003 | Kobe et al. |
| 6,743,211 B1 | 6/2004 | Prausnitz et al. |
| 6,743,581 B1 | 6/2004 | Vo-Dinh |
| 6,749,575 B2 | 6/2004 | Matriano et al. |
| 6,855,372 B2 | 2/2005 | Trautman et al. |
| 6,881,203 B2 | 4/2005 | Delmore et al. |
| 6,908,453 B2 | 6/2005 | Fleming et al. |
| 6,923,764 B2 | 8/2005 | Aceti et al. |
| 6,931,277 B1 | 8/2005 | Yuzhakov et al. |
| 6,945,952 B2 | 9/2005 | Kwon |
| 7,022,071 B2 | 4/2006 | Schaupp et al. |
| 7,045,069 B2 | 5/2006 | Ozeryansky |
| 7,048,723 B1 | 5/2006 | Frazier et al. |
| 7,097,631 B2 | 8/2006 | Trautman et al. |
| 7,169,600 B2 | 1/2007 | Hoss et al. |
| 7,211,062 B2 | 5/2007 | Kwon |
| 7,250,037 B2 | 7/2007 | Shermer et al. |
| 7,316,665 B2 | 1/2008 | Laurent et al. |
| 7,753,888 B2 | 7/2010 | Mukerjee et al. |
| 8,052,633 B2 | 11/2011 | Kendall |
| 8,062,573 B2 | 11/2011 | Kwon |
| 8,267,889 B2 | 9/2012 | Cantor et al. |
| 8,414,548 B2 | 4/2013 | Yuzhakov |
| 8,540,672 B2 | 9/2013 | McAllister |
| 8,734,697 B2 | 5/2014 | Chen et al. |
| 8,883,015 B2 | 11/2014 | Kendall et al. |
| 9,199,976 B2 | 12/2015 | Smythe et al. |
| 9,220,678 B2 | 12/2015 | Kendall et al. |
| 9,283,365 B2 | 3/2016 | Kendall et al. |
| 9,387,000 B2 | 7/2016 | Corrie et al. |
| 9,572,969 B2 | 2/2017 | Kendall |
| 10,422,881 B1 | 9/2019 | Wang et al. |
| 10,751,072 B2 | 8/2020 | Kendall |
| 11,029,287 B2 | 6/2021 | Wang et al. |
| 11,103,259 B2 * | 8/2021 | Crichton ............ A61B 17/205 |
| 11,147,954 B2 | 10/2021 | Junger et al. |
| 11,179,553 B2 | 11/2021 | Kendall et al. |
| 11,207,086 B2 | 12/2021 | Kendall |
| 2002/0008530 A1 | 1/2002 | Kim et al. |
| 2002/0016562 A1 | 2/2002 | Cormier et al. |
| 2002/0032415 A1 | 3/2002 | Trautman et al. |
| 2002/0128599 A1 | 9/2002 | Cormier et al. |
| 2002/0133129 A1 | 9/2002 | Arias et al. |
| 2002/0169411 A1 | 11/2002 | Sherman et al. |
| 2002/0177839 A1 | 11/2002 | Cormier et al. |
| 2003/0036710 A1 | 2/2003 | Matriano et al. |
| 2003/0199810 A1 | 10/2003 | Trautman et al. |
| 2003/0199811 A1 | 10/2003 | Sage, Jr. et al. |
| 2003/0202050 A1 | 10/2003 | Mrvos et al. |
| 2003/0220656 A1 * | 11/2003 | Gartstein ............ A61B 17/205 606/131 |
| 2004/0002121 A1 | 1/2004 | Regan et al. |
| 2004/0004649 A1 | 1/2004 | Bibl et al. |
| 2004/0008241 A1 | 1/2004 | Junhua |
| 2004/0039397 A1 | 2/2004 | Weber et al. |
| 2004/0049150 A1 * | 3/2004 | Dalton ............... A61K 39/00 604/46 |
| 2004/0087992 A1 | 5/2004 | Gartstein et al. |
| 2004/0161470 A1 | 8/2004 | Andrianov et al. |
| 2005/0042866 A1 | 2/2005 | Klapproth et al. |
| 2005/0089553 A1 | 4/2005 | Cormier et al. |
| 2005/0089554 A1 | 4/2005 | Cormier et al. |
| 2005/0126710 A1 | 6/2005 | Laermer et al. |
| 2005/0137531 A1 | 6/2005 | Prausnitz et al. |
| 2005/0143713 A1 | 6/2005 | Delmore et al. |
| 2005/0197308 A1 | 9/2005 | Dalton et al. |
| 2005/0261632 A1 | 11/2005 | Xu |
| 2006/0012780 A1 | 1/2006 | Nishiyama et al. |
| 2006/0015061 A1 | 1/2006 | Kuo et al. |
| 2006/0055724 A1 | 3/2006 | Krawczyk et al. |
| 2006/0074376 A1 | 4/2006 | Kwon |
| 2006/0195125 A1 | 8/2006 | Sakakine et al. |
| 2006/0202385 A1 * | 9/2006 | Xu .................. B81C 1/00111 425/542 |
| 2006/0264782 A1 | 11/2006 | Holmes et al. |
| 2007/0027474 A1 | 2/2007 | Lasner |
| 2007/0060867 A1 * | 3/2007 | Xu .................. A61K 9/0021 604/171 |
| 2007/0078376 A1 | 4/2007 | Smith |
| 2007/0224252 A1 | 9/2007 | Trautman et al. |
| 2007/0264749 A1 | 11/2007 | Birkmeyer |
| 2007/0270738 A1 | 11/2007 | Wu et al. |
| 2007/0293815 A1 | 12/2007 | Chan et al. |
| 2007/0299388 A1 | 12/2007 | Chan et al. |
| 2008/0009811 A1 | 1/2008 | Cantor |
| 2008/0108959 A1 | 5/2008 | Jung et al. |
| 2008/0114298 A1 | 5/2008 | Cantor et al. |
| 2008/0136874 A1 | 6/2008 | Tsukamura |
| 2008/0183144 A1 | 7/2008 | Trautman et al. |
| 2008/0245764 A1 | 10/2008 | Pirk et al. |
| 2008/0287858 A1 | 11/2008 | Duan |
| 2008/0312610 A1 | 12/2008 | Binks et al. |
| 2008/0312669 A1 | 12/2008 | Vries et al. |
| 2009/0017210 A1 | 1/2009 | Andrianov et al. |
| 2009/0041810 A1 | 2/2009 | Andrianov et al. |
| 2009/0198189 A1 | 8/2009 | Simons et al. |
| 2009/0292254 A1 * | 11/2009 | Tomono ............... A61P 3/10 264/293 |
| 2010/0221314 A1 | 9/2010 | Matsudo et al. |
| 2010/0222743 A1 | 9/2010 | Frederickson et al. |
| 2010/0256568 A1 | 10/2010 | Frederickson et al. |
| 2011/0021996 A1 | 1/2011 | Lee et al. |
| 2011/0028905 A1 | 2/2011 | Takada |
| 2011/0059150 A1 | 3/2011 | Kendall et al. |
| 2011/0160069 A1 | 6/2011 | Corrie et al. |
| 2011/0223542 A1 | 9/2011 | Kendall |
| 2011/0245776 A1 | 10/2011 | Kendall |
| 2011/0276027 A1 | 11/2011 | Trautman et al. |
| 2011/0288484 A1 | 11/2011 | Kendall et al. |
| 2012/0027810 A1 | 2/2012 | Chen et al. |
| 2012/0041412 A1 | 2/2012 | Roth et al. |
| 2012/0083741 A1 | 4/2012 | Kendall |
| 2012/0083762 A1 | 4/2012 | Kendall |
| 2012/0109065 A1 | 5/2012 | Backes |

(56) References Cited

U.S. PATENT DOCUMENTS

| | | |
|---|---|---|
| 2012/0136312 A1 | 5/2012 | Terahara et al. |
| 2012/0220981 A1 | 8/2012 | Soo et al. |
| 2012/0265141 A1 | 10/2012 | Kalpin et al. |
| 2012/0277629 A1 | 11/2012 | Bernstein et al. |
| 2012/0330250 A1 | 12/2012 | Kuwahara et al. |
| 2013/0079666 A1 | 3/2013 | Gonzalez-Zugasti et al. |
| 2013/0106964 A1 | 5/2013 | Rueby et al. |
| 2013/0131598 A1 | 5/2013 | Trautman et al. |
| 2013/0150822 A1 | 6/2013 | Ross |
| 2013/0158482 A1 | 6/2013 | Davis et al. |
| 2013/0190794 A1 | 7/2013 | Kendall et al. |
| 2013/0296790 A1 | 11/2013 | Masaoka et al. |
| 2013/0337150 A1 | 12/2013 | Biemans |
| 2014/0243747 A1 | 8/2014 | Tokumoto et al. |
| 2014/0257188 A1* | 9/2014 | Kendall ............ A61M 37/00 604/173 |
| 2014/0276366 A1 | 9/2014 | Bourne et al. |
| 2014/0276378 A1 | 9/2014 | Chen et al. |
| 2014/0276474 A1* | 9/2014 | Ding ............ A61P 29/00 604/289 |
| 2015/0057604 A1 | 2/2015 | Arami et al. |
| 2015/0080844 A1 | 3/2015 | Donovan et al. |
| 2016/0015952 A1 | 1/2016 | Omachi et al. |
| 2016/0058697 A1 | 3/2016 | Kendall et al. |
| 2016/0220803 A1 | 8/2016 | Kendall et al. |
| 2016/0265733 A1 | 9/2016 | Bauer et al. |
| 2016/0271381 A1* | 9/2016 | Falo, Jr. ............ B29C 39/025 |
| 2016/0310412 A1 | 10/2016 | Tanoue et al. |
| 2017/0014336 A1* | 1/2017 | Kuruma ............ A61P 31/16 |
| 2017/0056637 A1* | 3/2017 | Unger ............ A61M 37/0092 |
| 2017/0065804 A1* | 3/2017 | Uemura ............ B29C 37/0053 |
| 2017/0182301 A1 | 6/2017 | Kendall |
| 2017/0239458 A1* | 8/2017 | Kato ............ A61M 37/0015 |
| 2017/0282417 A1 | 10/2017 | Okano et al. |
| 2017/0296465 A1 | 10/2017 | Yoshida et al. |
| 2017/0361082 A1* | 12/2017 | Okano ............ A61M 37/0015 |
| 2017/0368322 A1 | 12/2017 | Kato et al. |
| 2018/0015271 A1 | 1/2018 | Junger et al. |
| 2018/0161050 A1 | 6/2018 | Kendall |
| 2018/0250503 A1* | 9/2018 | Enomoto ......... A61M 37/0015 |
| 2018/0264244 A1 | 9/2018 | Meliga et al. |
| 2018/0326726 A1 | 11/2018 | Wang et al. |
| 2019/0001109 A1* | 1/2019 | Kim ............ C08B 37/0072 |
| 2019/0046479 A1 | 2/2019 | Pathak |
| 2020/0246450 A1 | 8/2020 | Junger et al. |
| 2020/0246545 A1 | 8/2020 | Langer et al. |
| 2020/0368511 A1 | 11/2020 | Lemaire |
| 2020/0405331 A1 | 12/2020 | Kendall |
| 2021/0170152 A1 | 6/2021 | Kendall et al. |
| 2021/0244926 A1 | 8/2021 | Meliga et al. |
| 2021/0270599 A1 | 9/2021 | Junger et al. |

FOREIGN PATENT DOCUMENTS

| | | |
|---|---|---|
| CN | 101297989 A | 11/2008 |
| EP | 0 139 286 B1 | 8/1991 |
| EP | 0 732 208 A1 | 9/1996 |
| EP | 1 695 734 B1 | 6/2008 |
| EP | 2 213 284 A1 | 8/2010 |
| EP | 2 327 419 A1 | 6/2011 |
| EP | 2 568 174 A1 | 3/2013 |
| EP | 2 835 147 A1 | 2/2015 |
| JP | 2003-127430 A | 5/2003 |
| JP | 2007-260889 A | 10/2007 |
| JP | 2008114561 A | 5/2008 |
| JP | 2010-071845 A | 4/2010 |
| JP | 2013043034 A | 3/2013 |
| JP | 2016-166769 A | 9/2016 |
| WO | 91/06571 A1 | 5/1991 |
| WO | 94/24281 A1 | 10/1994 |
| WO | 98/28037 A1 | 7/1998 |
| WO | 98/28038 A1 | 7/1998 |
| WO | 99/02694 A1 | 1/1999 |
| WO | 99/42564 A2 | 8/1999 |
| WO | 99/64580 A1 | 12/1999 |
| WO | 00/05339 A1 | 2/2000 |
| WO | 00/42215 A1 | 7/2000 |
| WO | 00/74763 A2 | 12/2000 |
| WO | 00/74764 A1 | 12/2000 |
| WO | 01/03361 A1 | 1/2001 |
| WO | 01/33614 A1 | 5/2001 |
| WO | 01/85207 A2 | 11/2001 |
| WO | 02/064193 A2 | 8/2002 |
| WO | 02/074173 A1 | 9/2002 |
| WO | 02/075794 A2 | 9/2002 |
| WO | 02/085446 A2 | 10/2002 |
| WO | 02/085447 A2 | 10/2002 |
| WO | 02/100476 A2 | 12/2002 |
| WO | 03/020359 A2 | 3/2003 |
| WO | 03/026732 A2 | 4/2003 |
| WO | 03/048031 A2 | 6/2003 |
| WO | 03/053258 A1 | 7/2003 |
| WO | 03/092785 A1 | 11/2003 |
| WO | 2004/000389 A2 | 12/2003 |
| WO | 2004/024224 A1 | 3/2004 |
| WO | 2005/049108 A2 | 6/2005 |
| WO | 2005/060621 A2 | 7/2005 |
| WO | 2005/069736 A2 | 8/2005 |
| WO | 2005/072360 A2 | 8/2005 |
| WO | 2005/072630 A1 | 8/2005 |
| WO | 2005/123173 A1 | 12/2005 |
| WO | 2006/055799 A1 | 5/2006 |
| WO | 2006/101459 A1 | 9/2006 |
| WO | 2006/108185 A1 | 10/2006 |
| WO | 2006/116281 A2 | 11/2006 |
| WO | 2006/138719 A2 | 12/2006 |
| WO | 2007/002123 A2 | 1/2007 |
| WO | 2007/002521 A1 | 1/2007 |
| WO | 2007/012114 A1 | 2/2007 |
| WO | 2007/030477 A2 | 3/2007 |
| WO | 2007/054090 A1 | 5/2007 |
| WO | 2007/061781 A1 | 5/2007 |
| WO | 2007/061871 A1 | 5/2007 |
| WO | 2007/070004 A2 | 6/2007 |
| WO | 2007/080427 A2 | 7/2007 |
| WO | 2007/127976 A2 | 11/2007 |
| WO | 2008/010681 A1 | 1/2008 |
| WO | 2008/011625 A2 | 1/2008 |
| WO | 2008/053481 A1 | 5/2008 |
| WO | 2008/069566 A1 | 6/2008 |
| WO | 2008/083209 A2 | 7/2008 |
| WO | 2008/091602 A2 | 7/2008 |
| WO | 2009/040548 A1 | 4/2009 |
| WO | 2009/066763 A1 | 5/2009 |
| WO | WO 2009077859 A1 | 6/2009 |
| WO | 2009/079712 A1 | 7/2009 |
| WO | 2009/081122 A1 | 7/2009 |
| WO | 2009/097660 A1 | 8/2009 |
| WO | 2009/140735 A1 | 11/2009 |
| WO | 2010/042996 A1 | 4/2010 |
| WO | 2010/071918 A1 | 7/2010 |
| WO | 2010/109471 A1 | 9/2010 |
| WO | 2011/105496 A1 | 9/2011 |
| WO | 2011/116388 A1 | 9/2011 |
| WO | 2012/119907 A1 | 9/2012 |
| WO | 2012/122162 A1 | 9/2012 |
| WO | 2013/053022 A1 | 4/2013 |
| WO | 2013/055641 A1 | 4/2013 |
| WO | 2014/058746 A1 | 4/2014 |
| WO | 2015/034924 A1 | 3/2015 |
| WO | 2016/123665 A1 | 8/2016 |
| WO | 2016/143514 A1 | 9/2016 |
| WO | 2017/123652 A1 | 7/2017 |
| WO | 2018/119174 A1 | 6/2018 |

OTHER PUBLICATIONS

U.S. Appl. No. 17/089,446, filed Nov. 4, 2020, Delivery Device.
U.S. Appl. No. 15/849,134, filed Dec. 20, 2017, Delivery Device.
U.S. Appl. No. 16/896,387, filed Jun. 9, 2020, Delivery Device.
U.S. Appl. No. 17/326,064, filed May 20, 2021, Delivery Device.

(56) References Cited

OTHER PUBLICATIONS

U.S. Appl. No. 15/548,065, filed Aug. 1, 2017, Microprojection Array Applicator and Method.
U.S. Appl. No. 15/762,913, filed Mar. 23, 2018, Microprojection Arrays With Enhanced Skin Penetrating Properties and Methods Thereof.
U.S. Appl. No. 17/241,927, filed Apr. 27, 2021, Microprojection Arrays With Enhanced Skin Penetrating Properties and Methods Thereof.
U.S. Appl. No. 15/942,895, filed Apr. 2, 2018, Device and Method for Coating Surfaces.
U.S. Appl. No. 16/622,092, filed Dec. 12, 2019, Quality Control of Substrate Coatings.
U.S. Appl. No. 17/323,671, filed May 18, 2021, Quality Control of Substrate Coatings.
U.S. Appl. No. 16/636,467, filed Feb. 4, 2020, Compact High Mechanical Energy Storage and Low Trigger Force Actuator for the Delivery of Microprojection Array Patches (MAP).
U.S. Appl. No. 16/638,072, filed Feb. 10, 2020, Differential Coating of Microprojections and Microneedles on Arrays.
Desai et al., "Understanding release kinetics of biopolymer drug delivery microcapsules for biomedical applications," *Materials Science and Engineering B* 168:127-131, 2010.
Chinese Office Action dated Feb. 14, 2022 for Chinese Application No. 201880036675.8, 12 pages.
Japanese Office Action dated Feb. 8, 2022 for Japanese Application No. 2019-554394, 6 pages.
Aichele et al., "Antiviral Cytotoxic T Cell Response Induced by In Vivo Priming With a Free Synthetic Peptide," *J. Exp. Med.* 171:1815-1820, 1990.
Albert et al., "Dendritic cells acquire antigen from apoptotic cells and induce class I-restricted CTLs," *Nature* 392:86-89, 1998.
Albert et al., "Tumor-specific killer cells in paraneoplastic cerebellar degeneration," *Nature Medicine* 4(11):1321-1324, 1998.
Anderson, "Cutaneous Microdialysis: Is it Worth the Sweat?," *Journal of Investigative Dermatology* 126:1207-1209, 2006.
Athanasopoulos et al., "Gene therapy vectors based on adeno-associated virus: Characteristics and applications to acquired and inherited diseases (Review)," *International Journal of Molecular Medicine* 6:363-375, 2000.
Australian Examination Report No. 1 dated Oct. 9, 2020 for Australian Application No. 2016333148, 5 pages.
Australian Examination report No. 2 for standard patent application, dated Jan. 9, 2017, for Australian Application No. 2012323782, 4 pages.
Australian Patent Examination Report No. 1, dated Apr. 11, 2016, for Australian Application No. 2012323782, 3 pages.
Australian Patent Examination Report No. 1, dated Mar. 27, 2013, for Australian Application No. 2009212106, 5 pages.
Bachmann et al., "Dendritic cells process exogenous viral proteins and virus-like particles for class I presentation to $CD8^+$ cytotoxic T lymphocytes," *Eur. J. Immunol.* 26:2595-2600, 1996.
Boehm et al., "Inkjet printing for pharmaceutical applications," *Materials Today* 17(5):247-252, 2014.
Camilli et al., "*Listeria monocytogenes* Mutants Lacking Phosphatidylinositol-specific Phospholipase C Are Avirulent," *J. Exp. Med.* 173:751-754, 1991.
Canadian Office Action, dated Apr. 23, 2015, for Canadian Application No. 2,749,347, 4 pages.
Canadian Office Action, dated Feb. 17, 2015, for Canadian Application No. 2,745,339, 4 pages.
Chinese 1st Office Action, dated Feb. 17, 2012, for Chinese Application No. 200980104635.3, 13 pages. (with English Translation).
Chinese 2nd Office Action, dated Sep. 24, 2012, for Chinese Application No. 200980104635.3, 9 pages. (with English Translation).
Chinese 3rd Office Action, dated Dec. 28, 2012, for Chinese Application No. 200980104635.3, 6 pages. (with English Translation).
Chinese Office Action dated Jan. 11, 2021 for Chinese Application No. 201880036675.8, 31 pages. (w/ machine translation).
Communication pursuant to Article 94(3) EPC, dated Jan. 19, 2021, for European Application No. 16 746 000.5, 4 pages.
Cormier et al., "Transdermal delivery of desmopressin using a coated microneedle array patch system," *Journal of Controlled Release* 97:503-511, 2004.
Cox et al., "Adjuvants—a classification and review of their modes of action," *Vaccine* 15(3):248-256, 1997.
Crichton et al., "The effect of strain rate on the precision of penetration of short densely-packed microprojection array patches coated with vaccine," *Biomaterials* 31(16):4562-4572, 2010.
Crichton et al., "The viscoelastic, hyperelastic and scale dependent behaviour of freshly excised individual skin layers," Biomaterials 32:4670-4681, 2011.
Dreyer, "Microneedles: Microprocessing in Medicine," Final Presentation ENMA465 Project, May 10, 2004, URL=http://www.mse.umd.edu/undergrad/courses/ENMA465-project-results.html, 23 pages.
European Search Report dated Sep. 10, 2018, for European Application No. 16746000.5, 3 pages.
Extended European Search Report, dated Jul. 20, 2012, for European Application No. 09833918.7-1526, 9 pages.
Extended European Search Report, dated Nov. 10, 2015, for European Application No. 12840561.0-1506, 11 pages.
Extended European Search Report dated Nov. 30, 2020 for European Application No. 18 77 6793, 10 pages.
Extended European Search Report dated Feb. 15, 2021 for European Application No. 18 81 6698, 8 pages.
Extended European Search Report, dated Sep. 26, 2014, for European Application No. 09707729.1-1508, 9 pages.
Feng et al., "Molecular Biomarkers for Cancer Detection in Blood and Bodily Fluids," *Critical Reviews in Clinical Laboratory Sciences* 43(5-6):497-560, 2006.
Fernando et al., "Influenza nucleoprotein DNA vaccination by a skin targeted, dry coated, densely packed microprojection array (Nanopatch) induces potent antibody and CD8+ T cell responses," *Journal of Controlled Release* 237:35-41, 2016.
Fernando et al., "Potent Immunity to Low Doses of Influenza Vaccine by Probabilistic Guided Micro-Targeted Skin Delivery in a Mouse Model," PLoS One 5(4):e10266, 2010. (11 pages).
Fernando et al., "Safety, tolerability, acceptability and immunogenicity of an influenza vaccine delivered to human skin by a novel high-density microprojection array patch (Nanopatch™)," *Vaccine* 36:3779-3788, 2018.
Gao et al., "Priming of Influenza Virus-Specific Cytotoxic T Lymphocytes Vivo by Short Synthetic Peptides," *The Journal of Immunology* 147(10):3268-3273, 1991.
Garafalo et al., "Histamine release and therapy of severe dermatographism," *The Journal of Allergy and Clinical Immunology* 68(2):103-105, 1981.
Gardeniers et al., "Silicon Micromachined Hollow Microneedles for Transdermal Liquid Transport," *Journal of Microelectromechanical Systems* 12(6):855-862, 2003.
Gill et al., "Coated microneedles for transdermal delivery," *Journal of Controlled Release* 117(2):227-237, 2007.
Gill et al., "Coating Formulations for Microneedles," *Pharmaceutical Research* 24(7):1369-1380, 2007.
Henry et al., "Microfabricated Microneedles: A Novel Approach to Transdermal Drug Delivery," *Journal of Pharmaceutical Sciences* 87(8):922-925, 1998.
International Preliminary Report on Patentability dated Feb. 4, 2020 for International Application No. PCT/AU2018/050810, 9 pages.
International Preliminary Report on Patentability, dated Jun. 29, 2010, for International Application No. PCT/AU2008/001903, 7 pages.
International Preliminary Report on Patentability, dated Jun. 7, 2006, for International Application No. PCT/GB2005/000336, 9 pages.
International Preliminary Report on Patentability, dated Nov. 14, 2012, for International Application No. PCT/AU2011/000890, 6 pages.
International Search Report and Written Opinion, dated Dec. 6, 2016, for International Application No. PCT/AU2016/050867, 20 pages.

(56) References Cited

OTHER PUBLICATIONS

International Search Report and Written Opinion, dated Dec. 22, 2016, for International Application No. PCT/AU2016/050907, 14 pages.
International Search Report and Written Opinion, dated Feb. 20, 2009, for International Application No. PCT/AU2008/001903, 11 pages.
International Search Report and Written Opinion, dated Mar. 7, 2016, for International Application No. PCT/AU2016/050056, 13 pages.
International Search Report dated Aug. 1, 2018, for International Application No. PCT/AU2018/050586, 4 pages.
International Search Report, dated Feb. 20, 2013, for International Application No. PCT/AU2012/001289, 13 pages.
International Search Report dated Jul. 30, 2018, for International Application No. PCT/AU2018/050298, 6 pages.
International Search Report dated May 25, 2020 for International Application No. PCT/AU2020/050296, 6 pages.
International Search Report, dated Oct. 25, 2011, for International Application No. PCT/AU2011/000890, 4 pages.
International Search Report dated Nov. 8, 2018, for International Application No. PCT/AU2018/050810, 8 pages.
International Search Report dated Sep. 13, 2018, for International Application No. PCT/AU2018/050847, 4 pages.
Ito et al., "Evaluation of self-dissolving needles containing low molecular weight heparin (LMWH) in rats," *International Journal of Pharmaceutics* 349:124-129, 2008.
Ito et al., "Feasibility of microneedles for percutaneous absorption of insulin," *European Journal of Pharmaceutical Sciences* 29:82-88, 2006.
Ito et al., "Self-dissolving microneedles for the percutaneous absorption of EPO in mice," *Journal of Drug Targeting* 14(5):255-261, 2006.
Jondal et al., "MHC Class I-Restricted CTL Responses to Exogenous Antigens," *Immunity* 5:295-302, 1996.
Kay et al., "Viral vectors for gene therapy: the art of turning infectious agents into vehicles of therapeutics," *Nature Medicine* 7(1):33-40, 2001.
Kendall et al., "The mechanical properties of the skin epidermis in relation to targeted gene and drug delivery," *Biomaterials* 28:4968-4977, 2007.
Kuzu et al., "In vivo priming effect during various stages of ontogeny of an influenza A virus nucleoprotein peptide," *Eur. J. Immunol.* 23:1397-1400, 1993.
Kwon et al., "In Vitro Modeling of Transdermal PTH Delivery by Dissolving Micro-needle Patch," *34th Annual Meeting & Exposition of the Controlled Release Society*, Long Beach, California, USA, Jun. 5, 2007, 2 pages.
Kwon et al., "Rapid Intradermal Drug Delivery by a Dissolvable Micro-Needle Patch," *32nd Annual Meeting & Exposition of the Controlled Release Society*, Miami, Florida, USA, Jun. 18-22, 2005, 2 pages.
Kwon, "Acne Treatment by a Dissolvable Micro-Needle Patch," *33rd Annual Meeting & Exposition of the Controlled Release Society*, Vienna, Austria, Jul. 24, 2006, 2 pages.
Kwon, "In Vitro Evaluation of Transdermal Drug Delivery by a Micro-needle Patch," *31st Annual Meeting & Exposition of the Controlled Release Society*, Honolulu, Hawaii, USA, Jun. 12-16, 2004, 2 pages.
Lee et al., "Dissolving microneedles for transdermal drug delivery," *Biomaterials* 29:2113-2124, 2008.
Lin et al., "Silicon-Processed Microneedles," *IEEE Journal of Microelectromechanical Systems* 8(1):78-84, 1999.
Ma et al., "A PZT Insulin Pump Integrated with a Silicon Micro Needle Array for Transdermal Drug Delivery," *56th Electronic Components & Technology Conference*, San Diego, CA, May 30-Jun. 2, 2006, 5 pages.

Ma et al., "Coating solid dispersions on microneedles via a molten dip coating method: development and in vitro evaluation for transdermal delivery of a water insoluble drug," *J Pharm Sci* 103(11):3621-3630, 2014. (21 pages).
Matriano et al., "Macroflux® Microprojection Array Patch Technology: A New and Efficient Approach for Intracutaneous Immunization," *Pharmaceutical Research* 19(1):63-70, 2002.
Mengaud et al., "Expression in *Escherichia coli* and Sequence Analysis of the Listeriolysin O Determinant of *Listeria monocytogenes*," *Infection and Immunity* 56(4):766-772, 1988.
McAllister et al., "Microfabricated needles for transdermal delivery of macromolecules and nanoparticles: Fabrication methods and transport studies," *PNAS* 100(24):13755-13760, 2003.
Meléndez et al., "Thermal Inkjet Application in the Preparation of Oral Dosage Forms: Dispensing of Prednisolone Solutions and Polymorphic Characterization by Solid-State Spectroscopic Techniques," *Journal of Pharmaceutical Sciences* 97(7):2619-2636, 2008.
Miyano et al., "Hydrolytic Microneedles as Transdermal Drug Delivery System," *14th International Conference on Solid-State Sensors, Actuators and Microsystems*, Lyon, France, Jun. 10-14, 2007, pp. 355-358.
Miyano et al., "Sugar Micro Needles as Transdermic Drug Delivery System," *Biomedical Microdevices* 7(3):185-188, 2005.
Moore et al., "Introduction of Soluble Protein into the Class I Pathway of Antigen Processing and Presentation," *Cell* 54:777-785, 1988.
Mukerjee et al., "Microneedle array for transdermal biological fluid extraction and in situ analysis," *Sensors and Actuators A* 114:267-275, 2004.
Muller et al., "High-density microprojection array delivery to rat skin of low doses of trivalent inactivated poliovirus vaccine elicits potent neutralising antibody responses," *Scientific Reports* 7:12644, 2017. (10 pages).
Ng et al., "Potent response of QS-21 as a vaccine adjuvant in the skin when delivered with the Nanopatch, resulted in adjuvant dose sparing," *Scientific Reports* 6:29368, 2016. (12 pages).
Oh et al., "Demonstration of Dose-controlled Delivery by Dissolvable Micro-needle Arrays," *34th Annual Meeting & Exposition of the Controlled Release Society*, Long Beach, California, USA, Jun. 5, 2007, 2 pages.
Oh et al., "Intradermal influenza vaccine delivery using skin-penetrating dissolvable vaccine microneedles," *AAPS Annual Meeting and Exposition*, San Antonio, Texas, USA, Oct. 29-Nov. 2, 2006, 1 page.
Palmer et al., "Streptolysin O: A Proposed Model of Allosteric Interaction between a Pore-Forming Protein and Its Target Lipid Bilayer," *Biochemistry* 37:2378-2383, 1998.
Park et al., "Biodegradable polymer microneedles: Fabrication, mechanics and transdermal drug delivery," *Journal of Controlled Release* 104:51-66, 2005.
Park et al., "Polymer Microneedles for Controlled-Release Drug Delivery," *Pharmaceutical Research* 23(5):1008-1019, 2006.
Park et al., "Towards the silicon nanowire-based sensor for intracellular biochemical detection," *Biosensors and Bioelectronics* 22:2065-2070, 2007.
Portnoy et al., "Capacity of Listeriolysin O, Streptolysin O, and Perfringolysin O to Mediate Growth of *Bacillus subtilis* within Mammalian Cells," *Infection and Immunity* 60(7):2710-2717, 1992.
Radulescu et al., "Uniform Paclitaxel-Loaded Biodegradable Microspheres Manufactured by Ink-Jet Technology," *Proc., the Winter Symposium and 11th International Symposium on Recent Advantages in Drug-Delivery Systems, Controlled Release Society*, Salt Lake City, Utah, 2003, 5 pages.
Rossjohn et al., "Structure of a Cholesterol-Binding, Thiol-Activated Cytolysin and a Model of Its Membrane Form," *Cell* 89:685-692, 1997.
Sandler et al., "Inkjet Printing of Drug Substances and Use of Porous Substrates—Towards Individualized Dosing," *Journal of Pharmaceutical Sciences* 100(8):3386-3395, 2011.
Schulz et al., "Peptide-induced antiviral protection by cytotoxic T cells," *Proc. Natl. Acad. Sci. USA* 88:991-993, 1991.

(56) References Cited

OTHER PUBLICATIONS

Scoutaris et al., "Current Trends on Medical and Pharmaceutical Applications of Inkjet Printing Technology," *Pharm Res.* 33:1799-1816, 2016.

Scoutaris et al., "ToF-SIMS analysis of chemical heterogenities in inkjet micro-array printed drug/polymer formulations," *J Mater Sci: Mater Med* 23:385-391, 2012.

Silver et al., "Viscoelastic Properties of Young and Old Human Dermis: A Proposed Molecular Mechanism for Elastic Energy Storage in Collagen and Elastin," *J. Appl. Polym. Sci.* 86:1978-1985, 2002.

Stoeber et al., "Arrays of Hollow Out-of-Plane Microneedles for Drug Delivery," *Journal of Microelectromechanical Systems* 14(3):472-479, 2005.

Sullivan et al., "Minimally Invasive Protein Delivery with Rapidly Dissolving Polymer Microneedles," *Adv. Mater.* 20:933-938, 2008.

Tao et al., "A systematic study of dry etch process for profile control of silicon tips," *Microelectronic Engineering* 78-79:147-151, 2005.

Tarcha et al., "The Application of Ink-Jet Technology for the Coating and Loading of Drug-Eluting Stents," *Annals of Biomedical Engineering* 35(10):1791-1799, 2007.

Tsuchiya et al., "Development of Blood Extraction System for Health Monitoring System," *Biomedical Microdevices* 7(4):347-353, 2005.

Tyagi et al., "Molecular Beacons: Probes that Fluoresce upon Hybridization," *Nature Biotechnology* 14:303-308, 1996.

Vigna et al., "Lentiviral vectors: excellent tools for experimental gene transfer and promising candidates for gene therapy," *The Journal of Gene Medicine* 2:308-316, 2000.

Walther et al., "Viral Vectors for Gene Transfer: A Review of Their Use in the Treatment of Human Diseases," *Drugs* 60(2):249-271, 2000.

Wang et al., "Label-free hybridization detection of a single nucleotide mismatch by immobilization of molecular beacons on an agarose film," *Nucleic Acids Research* 30(12):e61, 2002. (9 pages).

Widera et al., "Effect of delivery parameters on immunization to ovalbumin following intracutaneous administration by a coated microneedle array patch system," *Vaccine* 24:1653-1664, 2006.

Wu et al., "Production of viral vectors for gene therapy applications," *Current Opinions in Biotechnology* 11:205-208, 2000.

Wu et al., "Solid free-form fabrication of drug delivery devices," *Journal of Controlled Release* 40:77-87, 1996.

Yuan et al., "Measuring microelastic properties of stratum corneum," *Colloids and Surfaces B: Biointerfaces* 48:6-12, 2006.

Zheng et al., "Multiplexed electrical detection of cancer markers with nanowire sensor arrays," *Nature Biotechnology* 23(10):1294-1301, 2005.

Zhou et al., "Liposome-Mediated Cytoplasmic Delivery of Proteins: An Effective Means of Accessing the MHC Class I-Restricted Antigen Presentation Pathway," Immunomethods 4:229-235, 1994.

\* cited by examiner

Fig. 6A  Fig. 6B

MICROPROJECTION ARRAYS WITH MICROPROJECTIONS HAVING LARGE SURFACE AREA PROFILES

BACKGROUND OF THE INVENTION

The invention is generally directed to devices and methods for intradermal delivery of active agents into the skin, more particularly, the invention is directed to devices and methods for improving the immunogenicity of vaccine preparations by intradermal delivery of the vaccine via a microprojection array in which the geometry of the projections have been designed to improve skin penetration.

DESCRIPTION OF THE PRIOR ART

In recent years, attempts have been made to devise new methods of delivering drugs and other bioactive materials, for vaccination and other purposes, which provide alternatives that are more convenient and/or enhanced in performance to the customary routes of administration such as intramuscular and intradermal injection. Limitations of injection include: cross-contamination through needle-stick injuries in health workers; injection phobia from a needle and syringe; and most importantly, as a result of its comparatively large scale and method of administration, the needle and syringe cannot target key cells in the outer skin layers. This is a serious limitation to many existing and emerging strategies for the prevention, treatment and monitoring of a range of untreatable diseases.

In response to the problems of needle and syringe, multiple devices and methods were developed to deliver active agents intradermally. Depending on the device the desired active agent can be applied either as a liquid formulation or as solid, powdered vaccine particles. The process of intradermal injection employs micron-sized needles that are inserted 1.5 mm perpendicularly into the skin, and which inject approximately 100-200 μl of a liquid vaccine formulation into the dermal skin layers. Microneedle arrays are made of coated solid microneedles or biodegradable microneedles. These are inserted into the dermal layers of the skin where either the coating is dissolved, or the microneedle itself dissolves in place.

In particular, the delivery of vaccines intradermally has presented challenges as the question of the ideal immune targeting location in the skin remains the subjection of debate. For example, Langerhans cells in the viable epidermis were considered to be immune cells until recently, however the prevailing thought is that these cells are tolerogenic (Romani, et al., J. Invest. Dermatol (2012) 132, 872). Intradermal injection is routinely shown to elicit strong immune responses and microprojection arrays such as the Nanopatch™ have demonstrated that reduced dosing utilizing these devices may be as effective as large dose intramuscular injection (Fernando, et al. PLos One (2010) 5, e10266). In addition to questions surrounding the ideal immune targeting location in the skin, the level of cellular/tissue damage caused by microprojection arrays is also an issue. This damage may be a large contributing factor to the immune response and the appropriate level of damage is an issue that is being explored. The mechanism of delivery of microprojection arrays to the skin also affects the level of cellular/tissue damage caused by microprojection arrays. Finally, due to the disparity in the mechanical modulus of the skin's constituent layers precise delivery of microprojection arrays to a targeted depth in the skin can be challenging.

There have been various approaches to optimizing the microneedle arrays and the methods by which they are made. Ceyssens et al., Fabrication process for tall, sharp, hollow high aspect ratio polymer microneedles on a platform, J. Micromech. and Microeng. 23 (2013) 075023 describes a process based on a combination of molding and UV lithography yielding hollow needles with record aspect ratio and sharpness that are monolithic with a platform, and feature a maximum needle length of over one millimeter while at the same time being suitable for mass fabrication. US Patent Publication No. 2009/0292254 disclose biocompatible and biodegradable microneedles having various shapes and geometries. U.S. Pat. No. 7,497,980 describes the manufacture of moulds for microneedles arrays are triangular as well as pyramidal and include microneedles that are solid as well as those through which a channel courses or those with grooves carved therein. U.S. Pat. No. 7,591,806 describes microblades or microdevices that are used as biological delivery devices that will puncture the skin. U.S. Pat. No. 6,537,264 discloses blade-type microneedles that are used to sample bodily fluids. US Patent Publication No. 2007/0293815 discloses microprojection arrays for penetrating the skin and delivering a vaccine. U.S. Pat. No. 8,414,548 describes microneedles that are formed from cutting metal with a laser and then bending the metal to form the microneedles. Prausnitz, M. R., Coated Microneedles for Transdermal Delivery, J. Controlled Release Soc. 117.2 (2007) 227-237 describe the use of sheet metal to fashion microneedles. US Patent Publication No. 2011/0021996 describes a microneedle array in which the microneedles have a conduit through which an active substance can be inserted into a body through the skin.

High density arrays require more energy to penetrate the skin than lower density arrays and thus modification to the shape, structure and geometry of the microprojections may be required to generate an efficient skin puncture that permits penetration of the microprojections to a greater depth within the skin. Therefore, there is a need to construct microprojection arrays with appropriate microprojection geometry coupled with an understanding of the mechanical parameters of vaccine placement, skin puncture and mechanically induced cellular damage so that a more efficient system of delivering vaccine to the skin may be provided. The microprojection arrays of the present invention provide devices with greater vaccine loading and delivery than previous designs with more precise targeting within the skin.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY OF THE PRESENT INVENTION

In a broad form the present invention seeks to provide a microprojection array comprising a substrate with a plurality of microprojections protruding from the substrate wherein the microprojections have a tapering hexagonal shape and comprise a tip and a base wherein the base has two substantially parallel sides with a slight draught angle of approximately 1 to 20 degrees up to a transition point at which point the angle increases to from about 20 degrees to about 70 degrees.

Typically the substrate is at least one of:
a) solid;
b) non-porous; and
c) non-hollow.

Typically the microprojection array includes a number of microprojections arranged in a line.

Typically the line is at least one of:
a) a straight line;
b) a curved line; and,
c) a circular line extending circumferentially around an axis.

Typically at least some of the microprojections in a line have a common base.

Typically the microprojection array includes a number of spaced apart lines.

Typically the spacing of the microprojections between adjacent lines is at least one of:
a) less than 200 µm;
b) less than 150 µm; and,
c) about 100 µm.

Typically the spacing between successive microprojections is at least one of:
a) less than 200 µm;
b) less than 150 µm;
c) less than 100 µm; and,
d) about 80 µm.

Typically the tip of each microprojection terminates in an elongate edge.

Typically the tip has a width of from about 1 µm to about 2 µm and a length of about 20 µm to about 2 mm.

Typically the tip has a width of about 1 µm and a length of about 20 µm.

Typically the base has a length of from about 30 µm to about 2 mm.

Typically the base has a length of about 80 µm.

Typically the base is greater in length than the tip.

Typically the base has a thickness of about 5 µm to 50 µm.

Typically the base has a cross sectional length:thickness aspect ratio of about 2:1 to 5:1.

Typically at least one of the microprojections is coated with a vaccine antigen.

Typically the amount of the vaccine antigen is about 10 ng to about 10 µg.

Typically the amount of vaccine antigen is about 10% to about 50% less than the amount of vaccine antigen delivered by intramuscular administration.

Typically the administration of the vaccine antigen provides a greater immunogenic response when administered to a human than a comparable amount of vaccine antigen administered by intramuscular injection.

Typically the administration of the vaccine antigen provides a greater immunogenic response when administered to a human than a comparable amount of vaccine antigen administered with a microprojection array with conical or cylindrical microprojections.

Typically the microprojections have an effective cross-sectional area which is unchanged by the addition of the coating.

In another broad form the present invention seeks to provide a method of administering a vaccine to a human comprising applying the microprojection array as described above to a human's skin.

Typically the microprojection array includes a number of microprojections arranged in a line, and wherein the method includes applying the microprojection array to a human's skin in a direction of movement including a component of movement aligned with the line.

Typically the line is a straight line and the method includes applying the microprojection array to the skin in a direction perpendicular to the skin and laterally parallel to the skin in the direction of the line.

Typically the line extends circumferentially around an axis and the method includes applying the microprojection array to the skin in a direction perpendicular to the skin whilst rotating the microprojection array around the axis.

In yet another broad form the present invention seeks to provide a microprojection array comprising a substrate with a plurality of microprojections protruding from the substrate wherein the microprojections have a tapering octagonal shape and comprise a tip and a base wherein the base has two substantially parallel sides with a slight draught angle of approximately 1 to 20 degrees up to a transition point at which point the angle increases to from about 20 degrees to about 70 degrees.

Typically the substrate is at least one of:
a) solid;
b) non-porous; and
c) non-hollow.

Typically the microprojection array includes a number of microprojections arranged in a line.

Typically the line is at least one of:
a) a straight line;
b) a curved line; and,
c) a circular line extending circumferentially around an axis.

Typically at least some of the microprojections in a line have a common base.

Typically the microprojection array includes a number of spaced apart lines.

Typically the spacing of the microprojections between adjacent lines is at least one of:
a) less than 200 µm;
b) less than 150 µm; and,
c) about 100 µm.

Typically the spacing between successive microprojections is at least one of:
a) less than 200 µm;
b) less than 150 µm;
c) less than 100 µm; and,
d) about 80 µm.

Typically the tip of each microprojection terminates in an elongate edge.

Typically the tip has a width of from about 1 µm to about 2 µm and a length of about 20 µm to about 2 mm.

BRIEF DESCRIPTION OF THE DRAWINGS

An example of the present invention will now be described with reference to the accompanying drawings, in which:—

FIG. 6A is a schematic front view of an example of a microprojection;

FIG. 6B is a schematic side view of the microprojection; and,

DETAILED DESCRIPTION OF THE PREFERRED EMBODIMENTS

Figure 1:
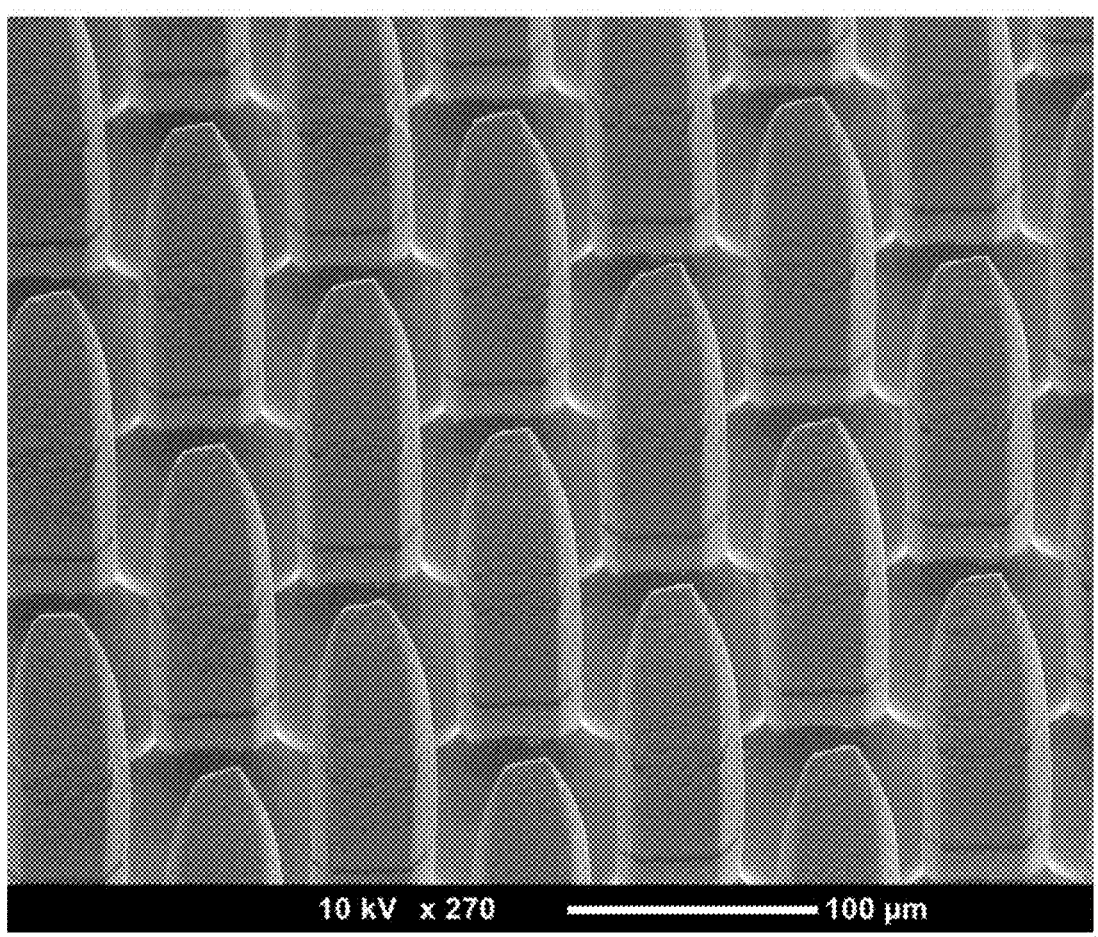
FIG. 1 is an SEM image of one embodiment of uncoated microprojections of the present invention.

The present invention relates to microprojection arrays where the microprojection design provides an alternative mode of skin puncture and vaccine delivery into the skin. The microprojections of the present invention are designed to have a large surface area to frontal profile design while maintaining a high density of microprojections on the array. The microprojection arrays of the present invention have a plurality of microprojections that are located upon a base. In one embodiment the microprojection have a shape that from a top down perspective is approximately an extended octagon. In another embodiment the microprojections have a shape that from a top down perspective is approximately an extended hexagon with two parallel sides being extended to give a rectangular profile with triangular ends (FIG. 1). The microprojections may be aligned in parallel lines with spacing between the edges of the microprojections. The microprojections may extend vertically to a length that will provide for drugs or vaccines to be delivered to the desired location within the skin. The microprojections of the microprojection arrays of the present invention may be solid or non-porous or contain hollow portions therein. In some embodiments the microprojections are solid and non-porous and do not contain any hollow portion therein. In preferred embodiments the devices of the present invention do not contain reservoirs.

At least a portion of the projections may be coated. Accordingly, one way of providing material for delivery to the biological subject is by providing the material within the coating. For example, the coating may include a vaccine for providing an immunological response within the subject. The coating may be provided in liquid or non-liquid forms, and may further include ingredients other than the material to be delivered, such as an adjuvant. Suitable coating formulations for use with projections patches and methods of applying such coatings to the projections are known, as described, for example, in WO/2010/042996 and WO/2009/079712.

Although any type of coating may be used, particularly advantageous embodiments of the microprojection arrays are provided with at least a portion of the projections coated with a non-liquid coating. In this regard, the term "non-liquid" coating will be understood to include a coating that is applied in a liquid form and allowed to dry or otherwise solidify to thereby form a non-liquid coating.

The non-liquid coating may act as an additional substantially solid layer of material which can be used to even further adjust the geometry of the projections by optionally causing the projections to have an effective profile of a different shape to the underlying uncoated profile of the projections as initially fabricated.

The microprojections of the present invention are less sensitive to coating thickness as it relates to skin penetration. In a standard conical projection the thickness of the coating affects the cross-sectional area of the microprojection thereby affecting the ability of the microprojection to penetrate the skin at a given velocity. In the microprojections of the present invention the effective cross-sectional area is little changed by the addition of the coating, thus the velocity required for skin penetration is relatively constant.

The microprojection arrays have a substrate with a plurality of microprojections protruding from the substrate wherein the microprojections have a tapering hexagonal shape and comprise a tip and a base wherein the base has two substantially parallel sides with a slight draught angle of approximately 1 to 20 degrees up to a transition point at which point the angle increases to from about 20 degrees to about 70 degrees. In an alternate embodiment the ends of the microprojections may be blunted to provide an extended octagonal profile. While the profiles of the microprojections of the present invention may define extended hexagonal or octagonal shapes the edges of the profiles may be somewhat rounded depending on the method of manufacture of the microprojections and microprojection arrays.

The draught angle may be between about 0 to 30 degrees or about 0 to 25 degrees or about 0 to 20 degrees or about 0 to 15 degrees or about 0 to 10 degrees, or about 1 to 30 degrees or about 1 to 25 degrees or about 1 to 20 degrees or about 1 to 15 degrees or about 1 to 10 degrees, or about 2 to 30 degrees or about 2 to 25 degrees or about 2 to 20 degrees or about 2 to 15 degrees or about 2 to 10 degrees, about 3 to 30 degrees or about 3 to 25 degrees or about 3 to 20 degrees or about 3 to 15 degrees or about 3 to 10 degrees, about 4 to 30 degrees or about 4 to 25 degrees or about 4 to 20 degrees or about 4 to 15 degrees or about 4 to 10 degrees, or about 5 to 30 degrees or about 5 to 25 degrees or about 5 to 20 degrees or about 5 to 15 degrees or about 5 to 10 degrees.

The transition point angle may be between about 20 to 70 degrees or about 20 to 65 degrees or about 20 to 60 degrees or about 20 to 55 degrees or about 20 to 50 degrees, or about 20 to 45 degrees or about 20 to 40 degrees or about 20 to 35 degrees or about 20 to 30 degrees or about 20 to 25 degrees, about 25 to 70 degrees or about 25 to 65 degrees or about 25 to 60 degrees or about 25 to 55 degrees or about 25 to 50 degrees, about 25 to 45 degrees or about 25 to 45 degrees or about 25 to 40 degrees or about 25 to 35 degrees or about 25 to 30 degrees, or about 30 to 70 degrees or about 30 to 65 degrees or about 30 to 60 degrees or about 30 to 55 degrees or about 30 to 50 degrees or about 30 to about 45 degrees or about 30 to about 40 degrees or about 30 to about 35 degrees. In preferred embodiments the transition point angle will be greater than the draught angle.

A sharp blade-like tip will allow for enhanced penetration of the microprojections into the skin while also generating an enhanced localized cell death/bystander interaction in the skin with a different profile than conical microprojection arrays. The sharp blade-like tips of the microprojections may also increase the level of danger signals and antigen to more live cells thereby increasing the physical adjuvant effect of microprojections and thereby improving immune responses. On a micro-scale, skin puncture is a function of crack formation in the skin and the subsequent expansion of these cracks. While high density microprojection arrays have each individual microprojection initiating a crack (which absorbs substantial energy), the microprojection arrays of the present invention provide a line of contact rather than a single point of contact. Thus, once the crack begins to form the microprojections may enter the skin more easily allowing internal skin surface area contract with the penetrating surface. Significantly more surface area of the protrusion can enter the skin without a large increase in energy. The microprojection profile of the microprojection arrays of the present invention is wider and thinner than current conical or circular microprojection profiles. The microprojection arrays of the present invention reduce the number of penetrations made upon entry to the skin, increase the area of the microprojection in the skin and exploit surface crack propagation to enhance overall penetration and reduce the overall energy required to puncture the skin. The microprojection array may be delivered to the skin surface by an applicator. Due to the unique design of the microprojections of the present invent invention the amount of energy required to penetrate the skin will be much less than that of other microprojection arrays. The microprojection arrays may be delivered by direct vertical application onto skin or a lateral movement on skin which will allow the blades of the microprojections to cut the skin.

While penetration of the skin by microprojections causes cell death, the microprojection arrays of the present invention provide a higher level of cell death per projection than the standard conical microprojection and generate significantly improved immune responses compared to the standard conical microprojection. Therefore, the microprojections of the present invention provide an increased and controlled physical adjuvantation effect in the skin thereby significantly improving immunogenicity.

The tip of the microprojections of the present invention may have a width of about 0.5 µm, or about 1.0 µm, or about 1.5 µm, or about 2.0 µm, or about 2.5 µm, or about 3.0 µm, or about 3.5 µm, or about 4.0 µm, or about 4.5 µm, or about 5.0 µm. The tip of the microprojections of the present invention may have a width of from about 0.5 µm to about 5.0 µm, or from about 0.5 µm to about 4.5 µm, or from about 0.5 µm to about 4.0 µm, or from about 0.5 µm to about 3.5 µm, or from about 0.5 µm to about 3.0 µm, or from about 0.5 µm to about 2.5 µm, or from about 0.5 µm to about 2.0 µm, or from about 0.5 µm to about 1.5 µm, or from about 0.5 µm to about 1.0 µm, or from about 1.0 µm to about 5.0 µm, or from about 1.0 µm to about 4.5 µm, or from about 1.0 µm to about 4.0 µm, or from about 1.0 µm to about 3.5 µm, or from about 1.0 µm to about 3.0 µm, or from about 1.0 µm to about 2.5 µm, or from about 1.0 µm to about 2.0 µm, or from about 1.0 µm to about 1.5 µm, or from about 1.5 µm to about 5.0 µm, or from about 1.5 µm to about 4.5 µm, or from about 1.5 µm to about 4.0 µm, or from about 1.5 µm to about 3.5 µm, or from about 1.5 µm to about 3.0 µm, or from about 1.5 µm to about 2.5 µm, or from about 1.5 µm to about 2.0 µm, or from about 2.0 µm to about 5.0 µm, or from about 2.0 µm to about 4.5 µm, or from about 2.0 µm to about 4.0 µm, or from about 2.0 µm to about 3.5 µm, or from about 2.0 µm to about 3.0 µm, or from about 2.0 µm to about 2.5 µm, or from about 2.5 µm to about 5.0 µm, or from about 2.5 µm to about 4.5 µm, or from about 2.5 µm to about 4.0 µm, or from about 2.5 µm to about 3.5 µm, or from about 2.5 µm to about 3.0 µm.

The tip of the microprojections of the present invention may have a length of about 20 µm, or about 30 µm, or about 40 µm, or about 50 µm, or about 60 µm, or about 70 µm, or about 80 µm, or about 90 µm, or about 100 µm, or about 150 µm, or about 200 µm, or about 250 nm, or about 500 nm, or about 1000 nm, or about 1500 nm, or about 2000 nm. The tip of the microprojections of the present invention may have a length of from about 10 µm to about 2 mm, or from about 10 µm to about 1.5 mm, or from about 10 µm to about 1 mm, or from about 10 µm to about 900 nm, or from about 10 µm to about 800 µm, or from about 10 µm to about 700 µm, or from about 10 µm to about 600 µm, or from about 10 µm to about 500 nm, or from about 10 µm to about 400 µm, or from about 10 µm to about 300 µm, or from about 10 µm to about 200 µm, or from about 10 µm to about 100 µm, or from about 10 µm to about 90 µm, or from about 10 µm to about 80 µm, or from about 10 µm to about 70 µm, or from about 10 µm to about 60 µm, or from about 10 µm to about 70 µm, or from about 10 µm to about 60 µm, or from about 10 µm to about 50 µm, or from about 10 µm to about 40 µm, or from about 10 µm to about 30 µm, or from about 10 µm to about 20 µm, or from about 20 µm to about 2 mm, or from about 20 µm to about 1.5 mm, or from about 20 µm to about 1 mm, or from about 20 µm to about 900 µm, or from about 20 µm to about 800 µm, or from about 20 µm to about 700 µm, or from about 20 µm to about 600 µm, or from about 20 µm to about 500 µm, or from about 20 µm to about 400 µm, or from about 20 µm to about 300 µm, or from about 20 µm to about 200 µm, or from about 20 µm to about 100 µm, or from about 20 µm to about 90 µm, or from about 20 µm to about 80 µm, or from about 20 µm to about 70 µm, or from about 20 µm to about 60 µm, or from about 20 µm to about 70 µm, or from about 20 µm to about 60 µm, or from about 20 µm to about 50 µm, or from about 20 µm to about 40 µm, or from about 20 µm to about 30 µm, about 30 µm to about 2 mm, or from about 30 µm to about 1.5 mm, or from about 30 µm to about 1 mm, or from about 30 µm to about 900 µm, or from about 30 µm to about 800 µm, or from about 30 µm to about 700 µm, or from about 30 µm to about 600 µm, or from about 30 µm to about 500 µm, or from about 30 µm to about 400 µm, or from about 30 µm to about 300 µm, or from about 30 µm to about 200 µm, or from about 30 µm to about 100 µm, or from about 30 µm to about 90 µm, or from about 30 µm to about 80 µm, or from about 30 µm to about 70 µm, or from about 30 µm to about 60 µm, or from about 30 µm to about 70 µm, or from about 30 µm to about 60 µm, or from about 30 µm to about 50 µm, or from about 30 µm to about 40 µm.

The base of the microprojections of the present invention may have a length of about 25 µm, or about 30 µm, or about 35 µm, or about 40 µm, or about 45 µm, or about 50 µm, or about 55 µm, or about 60 µm, or about 65 µm, or about 70 µm, or about 75 µm, or about 80 µm, or about 85 µm, or about 90 µm or about 100 µm or about 200 µm, or about 300 µm, or about 350 µm, or about 400 µm, or about 450 µm, or about 500 µm, or about 550 µm, or about 600 µm, or about 650 µm, or about 700 µm, or about 750 µm, or about 800 µm, or about 850 µm, or about 900 µm or about 1000 µm or about 1500 µm or about 2000 µm. The base of the microprojections of the present invention may have a length of from about 30 µm to about 2 mm, or from about 30 µm to about 1.5 mm, or from about 30 µm to about 1 mm, or from about 30 µm to about 900 µm, or from about 30 µm to about 800 µm, or from about 30 µm to about 700 µm, or from about 30 µm to about 600 µm, or from about 30 µm to about 500 µm, or from about 30 µm to about 400 µm, or from about 30 µm to about 300 µm, or from about 30 µm to about 200 µm, or from about 30 µm to about 100 µm, or from about 30 µm to about 90 µm, or from about 30 µm to about 80 µm, or from about 30 µm to about 70 µm, or from about 30 µm to about 60 µm, or from about 30 µm to about 70 µm, or from about 30 µm to about 60 µm, or from about 30 µm to about 50 µm, or from about 50 µm to about 1.5 mm, or from about 50 µm to about 1 mm, or from about 50 µm to about 900 µm, or from about 50 µm to about 800 µm, or from about 50 µm to about 700 µm, or from about 50 µm to about 600 µm, or from about 50 µm to about 500 µm, or from about 50 µm to about 400 µm, or from about 50 µm to about 300 µm, or from about 50 µm to about 200 µm, or from about 50 µm to about 100 µm, or from about 50 µm to about 90 µm, or from about 50 µm to about 80 µm, or from about 50 µm to about 70 µm, or from about 50 µm to about 60 µm, or from about 80 µm to about 1.5 mm, or from about 80 µm to about 1 mm, or from about 80 µm to about 900 µm, or from about 80 µm to about 800 µm, or from about 80 µm to about 700 µm, or from about 80 µm to about 600 µm, or from about 80 µm to about 500 µm, or from about 80 µm to about 400 µm, or from about 80 µm to about 300 µm, or from about 80 µm to about 200 µm, or from about 80 µm to about 100 µm, or from about 80 µm to about 90 µm.

The base of the microprojections of the present invention may have a thickness of about 5 µm, or about 10 µm, or about 15 µm, or about 20 µm, or about 25 µm, or about 30 µm, or about 35 µm, or about 40 µm, or about 45 µm, or about 50 µm, or about 55 µm, or about 60 µm, or about 65 µm, or about 70 µm, or about 75 µm, or about 80 µm, or about 85 µm, or about 90 µm or about 100 µm. The base of the microprojections of the present invention may have a thickness of from about 5 µm to about 100 µm, or from about 5 µm to about 95 µm, or from about 5 µm to about 90 µm, or from about 5 µm to about 85 µm, or from about 5 µm to about 80 µm, or from about 5 µm to about 75 µm, or from about 5 µm to about 70 µm, or from about 5 µm to about 65 µm, or from about 5 µm to about 60 µm, or from about 5 µm to about 55 µm, or from about 5 µm to about 50 µm, or from about 5 µm to about 45 µm, or from about 5 µm to about 40 µm, or from about 5 µm to about 35 µm, or from about 5 µm to about 30 µm, or from about 5 µm to about 25 µm, or from about 5 µm to about 20 µm, or from about 5 µm to about 15 µm, or from about 5 µm to about 10 µm, or from about 10 µm to about 100 µm, or from about 10 µm to about 95 µm, or from about 10 µm to about 90 µm, or from about 10 µm to about 85 µm, or from about 10 µm to about 80 µm, or from about 10 µm to about 75 µm, or from about 10 µm to about 70 µm, or from about 10 µm to about 65 µm, or from about 10 µm to about 60 µm, or from about 10 µm to about 55 µm, or from about 10 µm to about 50 µm, or from about 10 µm to about 45 µm, or from about 10 µm to about 40 µm, or from about 10 µm to about 35 µm, or from about 10 µm to about 30 µm, or from about 10 µm to about 25 µm, or from about 10 µm to about 20 µm, or from about 10 µm to about 15 µm, or from about 20 µm to about 100 µm, or from about 20 µm to about 95 µm, or from about 20 µm to about 90 µm, or from about 20 µm to about 85 µm, or from about 20 µm to about 80 µm, or from about 20 µm to about 75 µm, or from about 20 µm to about 70 µm, or from about 20 µm to about 65 µm, or from about 20 µm to about 60 µm, or from about 20 µm to about 55 µm, or from about 20 µm to about 50 µm, or from about 20 µm to about 45 µm, or from about 20 µm to about 40 µm, or from about 20 µm to about 35 µm, or from about 20 µm to about 30 µm, or from about 20 µm to about 25 µm, or from about 30 µm to about 100 µm, or from about 30 µm to about 95 µm, or from about 30 µm to about 90 µm, or from about 30 µm to about 85 µm, or from about 30 µm to about 80 µm, or from about 30 µm to about 75 µm, or from about 30 µm to about 70 µm, or from about 30 µm to about 65 µm, or from about 30 µm to about 60 µm, or from about 30 µm to about 55 µm, or from about 30 µm to about 50 µm, or from about 30 µm to about 45 µm, or from about 30 µm to about 40 µm, or from about 30 µm to about 35 µm.

The base of the microprojections of the present invention have a cross sectional length:thickness aspect ratio of about 3:2, 2:1, 3:1, 4:1, 5:1, 6:1, 7:1, 8:1, 9:1, between 3:2 to 9:1, between 3:2 to 8:1, between 3:2 to 7:1, between 3:2 to 6:1; between 3:2 to 5:1, between 3:2 to 4:1, between 3:2 to 3:1, between 2:1 to 9:1, between 2:1 to 8:1, between 2:1 to 7:1, between 2:1 to 6:1; between 2:1 to 5:1, between 2:1 to 4:1, between 3:1 to 9:1, between 3:1 to 8:1, between 3:1 to 7:1, between 3:1 to 6:1; between 3:1 to 5:1, between 3:1 to 4:1, between 4:1 to 9:1, between 4:1 to 8:1, between 4:1 to 7:1, between 4:1 to 6:1; between 4:1 to 5:1, between 5:1 to 9:1, between 5:1 to 8:1, between 5:1 to 7:1, between 5:1 to 6:1, between 6:1 to 9:1, between 6:1 to 8:1, between 6:1 to 7:1, between 7:1 to 9:1, between 7:1 to 8:1, between 8:1 to 9:1. In this regard, a high aspect ratio can assist in having the projections penetrate the skin with minimal force. On a micro-scale, puncture is a function of crack formation and subsequent growth. The use of a high aspect ratio can assist in allowing cracks to form, thereby reducing the barrier to entry, whilst also maximising the surface area of the projections, which in turn maximises the amount of coating and hence payload that can be delivered. This means that significantly more surface area of the protrusion can enter the skin, without a large increase in energy.

The height of the microprojections of the present invention depends upon the depth of penetration required. The height of the microprojections of the present invention may have a length of from about 30 µm to about 2 mm, or from about 30 µm to about 1.5 mm, or from about 30 µm to about 1 mm, or from about 30 µm to about 900 µm, or from about 30 µm to about 800 µm, or from about 30 µm to about 700 µm, or from about 30 µm to about 600 µm, or from about 30 µm to about 500 µm, or from about 30 µm to about 400 µm, or from about 30 µm to about 300 µm, or from about 30 µm to about 200 µm, or from about 30 µm to about 100 µm, or from about 30 µm to about 90 µm, or from about 30 µm to about 80 µm, or from about 30 µm to about 70 µm, or from about 30 µm to about 60 µm, or from about 30 µm to about 70 µm, or from about 30 µm to about 60 µm, or from about 30 µm to about 50 µm, or from about 50 µm to about 1.5 mm, or from about 50 µm to about 1 mm, or from about 50 µm to about 900 µm, or from about 50 µm to about 800 µm, or from about 50 µm to about 700 µm, or from about 50 µm to about 600 µm, or from about 50 µm to about 500 µm, or from about 50 µm to about 400 µm, or from about 50 µm to about 300 µm, or from about 50 µm to about 200 µm, or from about 50 µm to about 100 µm, or from about 50 µm to about 90 µm, or from about 50 µm to about 80 µm, or from about 50 µm to about 70 µm, or from about 50 µm to about 60 µm, or from about 80 µm to about 1.5 mm, or from about 80 µm to about 1 mm, or from about 80 µm to about 900 µm, or from about 80 µm to about 800 µm, or from about 80 µm to about 700 µm, or from about 80 µm to about 600 µm, or from about 80 µm to about 500 µm, or from about 80 µm to about 400 µm, or from about 80 µm to about 300 µm, or from about 80 µm to about 200 µm, or from about 80 µm to about 100 µm, or from about 80 µm to about 90 µm.

The density of the microprojection on the microprojection arrays may be about 2000 microprojections/cm$^2$, or about 2500 microprojections/cm$^2$, or about 3000 microprojections/cm$^2$, or about 3500 microprojections/cm$^2$, or about 4000 microprojections/cm$^2$, or about 4500 microprojections/cm$^2$, or about 5000 microprojections/cm$^2$, or about 5500 microprojections/cm$^2$, or about 6000 microprojections/cm$^2$, or about 6500 microprojections/cm$^2$, or about 7000 microprojections/cm$^2$, or about 7500 microprojections/cm$^2$, or about 8000 microprojections/cm$^2$, or about 8500 microprojections/cm$^2$, or about 9000 microprojections/cm$^2$, or about 9500 microprojections/cm$^2$, or about 10000 microprojections/cm$^2$, or about 11000 microprojections/cm$^2$, or about 12000 microprojections/cm$^2$, or about 13000 microprojections/cm$^2$, or about 14000 microprojections/cm$^2$, or about 15000 microprojections/cm$^2$, or about 16000 microprojections/cm$^2$, or about 17000 microprojections/cm$^2$, or about 18000 microprojections/cm$^2$, or about 19000 microprojections/cm$^2$, or about 20000 microprojections/cm$^2$. The density of the microprojection on the microprojection arrays may be from about 2000 to about 20000 microprojections/cm², or from about 2000 to about 15000 microprojections/cm², or from about to about 10000 microprojections/cm², or from about 2000 to about 9000 microprojections/cm², or from about 2000 to about 8000 microprojections/cm², or from about 2000 to about 7500 microprojections/cm², or from about 2000 to about 7000 microprojections/cm², or from about 2000 to about 6000 microprojections/cm², or from about 2000 to about 5000 microprojections/cm², or from about 2000 to about 4000 microprojections/cm², or from about 3000 to about 20000 microprojections/cm², or from about 3000 to about 15000 microprojections/cm², or from about to about 10000 microprojections/cm², or from about 3000 to about 9000 microprojections/cm², or from about 3000 to about 8000 microprojections/cm², or from about 3000 to about 7500 microprojections/cm², or from about 3000 to about 7000 microprojections/cm², or from about 3000 to about 6000 microprojections/cm², or from about 3000 to about 5000 microprojections/cm², or from about 3000 to about 4000 microprojections/cm², or from about 4000 to about 20000 microprojections/cm², or from about 4000 to about 15000 microprojections/cm², or from about to about 10000 microprojections/cm², or from about 4000 to about 9000 microprojections/cm², or from about 4000 to about 8000 microprojections/cm², or from about 4000 to about 7500 microprojections/cm², or from about 4000 to about 7000 microprojections/cm², or from about 4000 to about 6000 microprojections/cm², or from about 4000 to about 5000 microprojections/cm², or from about 5000 to about 20000 microprojections/cm², or from about 5000 to about 15000 microprojections/cm², or from about to about 10000 microprojections/cm², or from about 5000 to about 9000 microprojections/cm², or from about 5000 to about 8000 microprojections/cm², or from about 5000 to about 7500 microprojections/cm², or from about 5000 to about 7000 microprojections/cm², or from about 5000 to about 6000 microprojections/cm².

In one embodiment of the microprojections of the present invention the microprojections have a vertical shape that has an extruded base profile with a slight draught angle of approximately 0 to 20 degrees up to a transition point at which point the upper tip of the microprojection will slope towards the tip line at a greater angle.

The microprojection arrays of the present invention are comprised of a plurality of microprojections. The microprojections may be arrayed in lines. The spacing between microprojections on a single line may be from about 10 μm to about 500 μm, or from about 10 μm to about 450 μm or from about 10 μm to about 400 μm of from about 10 μm to about 350 μm or from about 10 μm to about 300 μm or from about 10 μm to about 250 μm; or from about 10 μm to about 200 μm of from about 10 μm to about 150 μm or from about 10 μm to about 100 μm or from about 10 μm to about 50 μm; or from about 20 μm to about 500 μm, or from about 20 μm to about 450 μm or from about 20 μm to about 400 μm of from about 20 μm to about 350 μm or from about 20 μm to about 300 μm or from about 20 μm to about 250 μm; or from about 20 μm to about 200 μm of from about 20 μm to about 150 μm or from about 20 μm to about 100 μm or from about 20 μm to about 50 μm; or from about 30 μm to about 500 μm, or from about 30 μm to about 450 μm or from about 30 μm to about 400 μm of from about 30 μm to about 350 μm or from about 30 μm to about 300 μm or from about 30 μm to about 250 μm; or from about 30 μm to about 200 μm of from about 30 μm to about 150 μm or from about 30 μm to about 100 μm or from about 30 μm to about 50 μm; or from about 40 μm to about 500 μm, or from about 40 μm to about 450 μm or from about 40 μm to about 400 μm of from about 40 μm to about 350 μm or from about 40 μm to about 300 μm or from about 40 μm to about 250 μm; or from about 40 μm to about 200 μm of from about 40 μm to about 150 μm or from about 40 μm to about 100 μm or from about 40 μm to about 50 μm; or from about 50 μm to about 500 μm, or from about 50 μm to about 450 μm or from about 50 μm to about 400 μm of from about 50 μm to about 350 μm or from about 50 μm to about 300 μm or from about 50 μm to about 250 μm; or from about 50 μm to about 200 μm of from about 50 μm to about 150 μm or from about 50 μm to about 100 μm. The spacing between lines of microprojections 40 μm to about 500 μm, or from about 40 μm to about 450 μm or from about 40 μm to about 400 μm of from about 40 μm to about 350 μm or from about 40 μm to about 300 μm or from about 40 μm to about 250 μm; or from about 40 μm to about 200 μm of from about 40 μm to about 150 μm or from about 40 μm to about 100 μm; or from about 50 μm to about 500 μm, or from about 50 μm to about 450 μm or from about 50 μm to about 400 μm of from about 50 μm to about 350 μm or from about 50 μm to about 300 μm or from about 50 μm to about 250 μm; or from about 50 μm to about 200 μm of from about 50 μm to about 150 μm or from about 50 μm to about 100 μm; or from about 75 μm to about 500 μm, or from about 75 μm to about 450 μm or from about 75 μm to about 400 μm of from about 75 μm to about 350 μm or from about 75 μm to about 300 μm or from about 75 μm to about 250 μm; or from about 75 μm to about 200 μm of from about 75 μm to about 150 μm.

In one embodiment of the present invention the microprojection has a tapering extended hexagonal shape with a rapidly tapering tip at the distal end. The microprojections have a spacing of 100 μm between adjacent lines and 80 μm between successive microprojections on the array (density about 8000/cm²). The tip of the protrusions tapers to a distal line of approximately 25 μm long and 1-2 μm wide.

A gas jet coating process may be used to deposit liquid vaccine material in the coating solution onto the projection array. The process parameters (i.e. jet angle, jet velocity, solution viscosity, etc.) of the coating method can affect the degree to which the coating material is localized towards the tips of the projections, rather than the base. In addition to these process parameters, coating of the liquid material to the projections can be further enhanced by modifying the surface properties of the projections relative to the liquid coating material. The coating may be applied using a gas jet coating technique as described in WO/2009/079712. The microprojection arrays of the present invention may penetrate further into the skin than corresponding arrays with conical or cylindrical microprojections having the same length and delivered with the same energy. The microprojection arrays of the present invention may penetrate further by 10% or 20% or 30% or 40% or 50% or 60% or 70% or 80% or 90% or 100%. The microprojection arrays of the present invention may penetrate further by 10% to 200% or from 10% to 150% or from 10% to 100% or from 10% to 90% or from 10% to 80% or from 10% to 70% or from 10% to 60% or from 10% to 50% or from 10% to 40% or from 10% to 30% or from 10% to 20% or from 20% to 200% or from 20% to 150% or from 20% to 100% or from 20% to 90% or from 20% to 80% or from 20% to 70% or from 20% to 60% or from 20% to 50% or from 20% to 40% or from 20% to 30% or from 30% to 200% or from 30% to 150% or from 30% to 100% or from 30% to 90% or from 30% to 80% or from 30% to 70% or from 30% to 60% or from 30% to 50% or from 30% to 40% or from 40% to 200% or from 40% to 150% or from 40% to 100% or from 40% to 90% or from 40% to 80% or from 40% to 70% or from 40% to 60% or from 40% to 50% or from 50% to 200% or from 50% to 150% or from 50% to 100% or from 50% to 90% or from 50% to 80% or from 50% to 70% or from 50% to 60%.

The microprojection arrays of the present invention may provide greater cell death in the cells surrounding the microprojections in the skin than corresponding arrays with conical or cylindrical microprojections having the same length and delivered with the same energy. The microprojection arrays of the present invention may provide cell death that is 10% or 20% or 30% or 40% or 50% or 60% or 70% or 80% or 90% or 100% greater. The microprojection arrays of the present invention may provide greater cell death by 10% to 200% or from 10% to 150% or from 10% to 100% or from 10% to 90% or from 10% to 80% or from 10% to 70% or from 10% to 60% or from 10% to 50% or from 10% to 40% or from 10% to 30% or from 10% to 20% or from 20% to 200% or from 20% to 150% or from 20% to 100% or from 20% to 90% or from 20% to 80% or from 20% to 70% or from 20% to 60% or from 20% to 50% or from 20% to 40% or from 20% to 30% or from 30% to 200% or from 30% to 150% or from 30% to 100% or from 30% to 90% or from 30% to 80% or from 30% to 70% or from 30% to 60% or from 30% to 50% or from 30% to 40% or from 40% to 200% or from 40% to 150% or from 40% to 100% or from 40% to 90% or from 40% to 80% or from 40% to 70% or from 40% to 60% or from 40% to 50% or from 50% to 200% or from 50% to 150% or from 50% to 100% or from 50% to 90% or from 50% to 80% or from 50% to 70% or from 50% to 60%.

The microprojection arrays of the present invention may provide increased immunogenicity as compared to intramuscular administration of vaccine. The microprojection arrays of the present invention may provide increased immunogenicity as compared to corresponding arrays with conical or cylindrical microprojections having the same length and delivered with the same energy in delivering vaccines. The microprojection arrays of the present invention may provide an increased immunogenic response by 10% or 20% or 30% or 40% or 50% or 60% or 70% or 80% or 90% or 100%. The microprojection arrays of the present invention may provide an increased immunogenic response by 10% to 200% or from 10% to 150% or from 10% to 100% or from 10% to 90% or from 10% to 80% or from 10% to 70% or from 10% to 60% or from 10% to 50% or from 10% to 40% or from 10% to 30% or from 10% to 20% or from 20% to 200% or from 20% to 150% or from 20% to 100% or from 20% to 90% or from 20% to 80% or from 20% to 70% or from 20% to 60% or from 20% to 50% or from 20% to 40% or from 20% to 30% or from 30% to 200% or from 30% to 150% or from 30% to 100% or from 30% to 90% or from 30% to 80% or from 30% to 70% or from 30% to 60% or from 30% to 50% or from 30% to 40% or from 40% to 200% or from 40% to 150% or from 40% to 100% or from 40% to 90% or from 40% to 80% or from 40% to 70% or from 40% to 60% or from 40% to 50% or from 50% to 200% or from 50% to 150% or from 50% to 100% or from 50% to 90% or from 50% to 80% or from 50% to 70% or from 50% to 60%.

The ability of the microprojection arrays of the present invention to provide a greater immunogenic response allows the microprojection arrays to deliver a lesser amount of vaccine to achieve the appropriate response as compared to intramuscular or intradermal administration by a needle. The ability of the microprojection arrays of the present invention to provide a greater immunogenic response allows the microprojection arrays to deliver a lesser amount of vaccine to achieve the appropriate response as compared to corresponding arrays with conical or cylindrical microprojection. Such "dose-sparing" benefit of the microprojection arrays permits a lesser amount of vaccine to be used in each dose to achieve the same immunogenic response. The amount of vaccine used with the microprojection arrays of the present invention may be 0.01%, 0.05%, 0.10%, 0.50%, 1%, 5% or 10% or 20% or 30% or 40% or 50% or 60% or 70% or 80% or 90% less than the amount of vaccine used in conventional vaccine administrations. The amount of vaccine used with the microprojection arrays of the present invention may be about 0.01% to 90% or from 0.01% to 80% or from 0.01% to 70% or from 0.01% to 60% or from 0.01% to 50% or from 0.01% to 40% or from 0.01% to 30% or from 0.01% to 20% or from 0.01% to 10% or from 0.01% to 1% or from 0.01% to 0.10% or from 0.05% to 90% or from 0.05% to 80% or from 0.05% to 70% or from 0.05% to 60% or from 0.05% to 50% or from 0.05% to 40% or from 0.05% to 30% or from 0.05% to 20% or from 0.05% to 10% or from 0.05% to 1% or from 0.05% to 0.10% or from 0.10% to 90% or from 0.10% to 80% or from 0.10% to 70% or from 0.10% to 60% or from 0.10% to 50% or from 0.10% to 40% or from 0.10% to 30% or from 0.10% to 20% or from 0.10% to 10% or from 0.10% to 1% or from 1% to 90% or from 1% to 80% or from 1% to 70% or from 1% to 60% or from 1% to 50% or from 1% to 40% or from 1% to 30% or from 1% to 20% or from 1% to 10% or from 5% to 90% or from 5% to 80% or from 5% to 70% or from 5% to 60% or from 5% to 50% or from 5% to 40% or from 5% to 30% or from 5% to 20% or from 5% to 10% or from 10% to 90% or from 10% to 80% or from 10% to 70% or from 10% to 60% or from 10% to 50% or from 10% to 40% or from 10% to 30% or from 10% to 20% or from 20% to 90% or from 20% to 80% or from 20% to 70% or from 20% to 60% or from 20% to 50% or from 20% to 40% or from 20% to 30% or from 30% to 90% or from 30% to 80% or from 30% to 70% or from 30% to 60% or from 30% to 50% or from 30% to 40% or from 40% to 90% or from 40% to 80% or from 40% to 70% or from 40% to 60% or from 40% to 50% or from 50% to 90% or from 50% to 80% or from 50% to 70% or from 50% to 60%.

The amount of vaccine antigen given per dose may be from about 1 ng, 5 ng, 10 ng, 20 ng, 30 ng, 40 ng, 50 ng, 60 ng, 70 ng, 80 ng, 90 ng, 100 ng, 250 ng, 500 ng, 750 ng, 1 μg dose, 2 μg dose, 3 μg dose, 4 μg dose, 5 μg dose, 6 μg dose, 7 μg dose, 8 μg dose, 9 μg dose, 10 μg dose, 15 μg dose, 20 μg dose, 25 μg dose, 30 μg, 40 μg dose, 50 μg dose, 60 μg dose, 70 μg dose, 80 μg dose may be sufficient to induce an immune response. The dose of vaccine antigen may be administered to the human within a range of doses including from about 1 ng to about 10 μg, about 1 ng to about 5 μg, about 1 ng to about 1 μg, about 1 ng to about 900 ng, about 1 ng to about 800 ng, about 1 ng to about 700 ng, about 1 ng to about 600 ng, about 1 ng to about 500 ng, about 1 ng to about 400 ng, about 1 ng to about 300 ng, about 1 ng to about 200 ng, about 1 ng to about 100 ng, about 1 ng to about 75 ng, about 1 ng to about 50 ng, about 1 ng to about 25 ng, about 10 ng to about 10 μg, about 10 ng to about 5 μg, about 10 ng to about 1 μg, about 10 ng to about 900 ng, about 10 ng to about 800 ng, about 10 ng to about 700 ng, about 10 ng to about 600 ng, about 10 ng to about 500 ng, about 10 ng to about 400 ng, about 10 ng to about 300 ng, about 10 ng to about 200 ng, about 10 ng to about 100 ng, about 10 ng to about 75 ng, about 10 ng to about 50 ng, about 10 ng to about 25 ng, about 0.1 μg to about 500 μg, 1 μg to about 100 μg, 1 μg to about 50 μg, from about 1 μg to about 30 μg, from about 1 μg to about 25 μg, from about 1 μg to about 20 μg, from about 1 μg to about 15 μg, from about 1 μg to about 10 μg, from about 2 μg to about 50 μg, 2 μg to about 30 μg, from about 2 µg to about 20 µg, from about 2 µg to about 10 µg, from about 2 µg to about 8 µg, from about 3 µg to about 50 µg, 3 µg to about 30 µg, from about 3 µg to about 20 µg, from about 3 µg to about 10 µg, from about 3 µg to about 8 µg, from about 3 µg to about 5 µg, from about 4 µg to about 50 µg, 4 µg to about 30 µg, from about 4 µg to about 20 µg, from about 4 µg to about 10 µg, from about 4 µg to about 8 µg, from about 5 µg to about 50 µg, 5 µg to about 30 µg, from about 5 µg to about 20 µg, from about 5 µg to about 10 µg, from about 5 µg to about 9 µg, and from about 5 µg to about 8 µg.

The microprojection array may be applied vertically, laterally or a combination thereof. A lateral application of the microprojection array will slide the microprojections along the surface of the skin to penetrate the skin in lanes.

The applicators of the present invention utilize a 'low-force, higher velocity' applicator which may use a "flying" microprojection array in which the microprojection array is discharged from the device with sufficient force to propel the array through space and into the skin. Peak stresses are associated with the penetration of projections, without the follow-through, and the higher velocity achieves the change of behavior of the skin from elastic to plastic. The use of low force, high velocity approach to penetration of the skin by the microprojection array provides advantages such as: achieving equivalent penetration in the skin, but with about only $1/10^{th}$ the Kinetic Energy; improved patient acceptability/tolerability of the penetration of the skin by the microprojection array and significantly less breakage of projections (up to about $1/10000$ reduction of breakage) and patch base. The use of low force, high velocity application of the microprojection array to the skin also provides consistent penetration of the patch from site to site, because the mechanics of penetration are not heavily reliant on variations of the subcutaneous tissue (which does vary significantly within and individual and between people in populations). The direct correlation of kinetic energy with penetration may be utilized to design an applicator and microarray projections that provides maximal efficiency in delivering material to the patient while reducing discomfort to the patient.

The speed of the microprojection array as it is projected into the skin depends at least in part upon the density of the projections in the microarray and the area of the array. The range of speeds for the microprojection array entering the skin may be from about 5 m/s to about 50 m/s or from about 5 m/s to about 40 m/s or from about 5 m/s to about 30 m/s or from about 5 m/s to about 25 m/s or from about 5 m/s to about 20 m/s or about 10 m/s to about 50 m/s or from about 10 m/s to about 40 m/s or from about 10 m/s to about 30 m/s or from about 10 m/s to about 25 m/s or from about 10 m/s to about 20 m/s or from about 20 m/s to about 50 m/s or from about 20 m/s to about 40 m/s or from about 20 m/s to about 30 m/s or from about 25 m/s to about 50 m/s or from about 25 m/s to about 40 m/s or from about 25 m/s to about 30 m/s. In preferred embodiments of the of the present invention the speed of the microprojection array is at least 15 m/s or at least 20 m/s or at least 25 m/s or at least 30 m/s.

In one embodiment the microprojections have a tapering extended hexagonal shape with a rapidly tapering tip at the distal end. The protrusions have a spacing of 100 µm between adjacent lines and 80 µm between successive protrusions (density about 8000/cm$^2$). The tip of the protrusions tapers to a distal line of approximately 25 µm long and 1-2 µm wide.

Figure 5A:
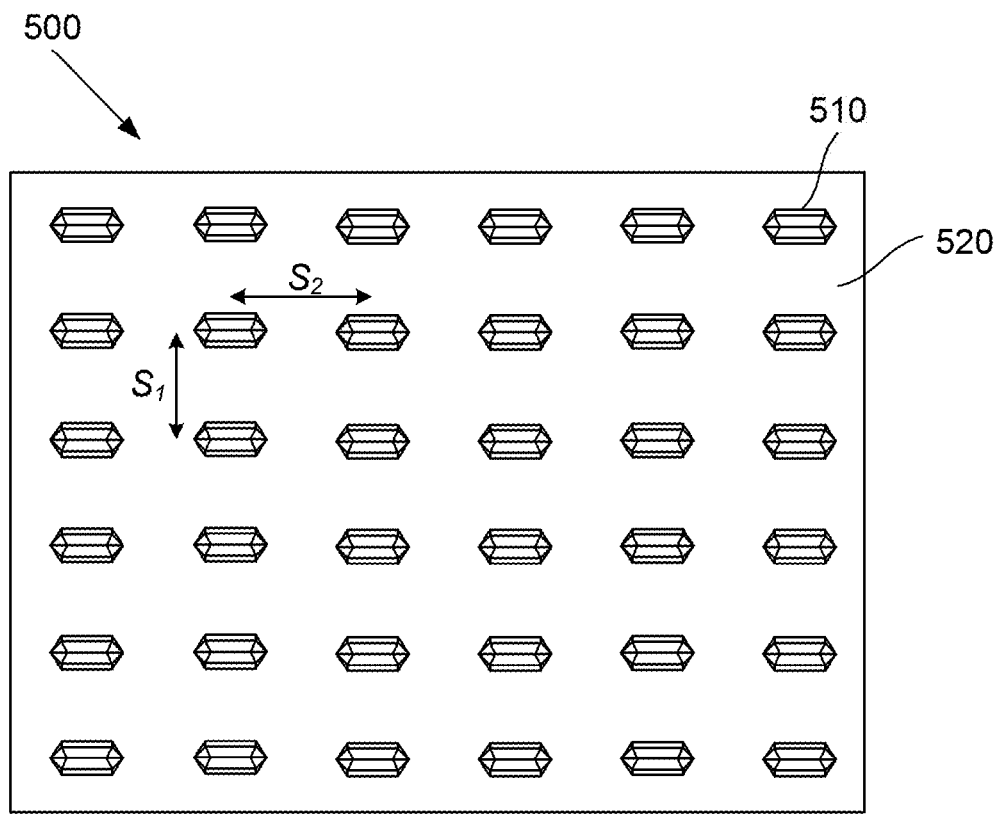
FIG. 5A is a schematic plan view of an example of a microprojection array.
Figure 5B:
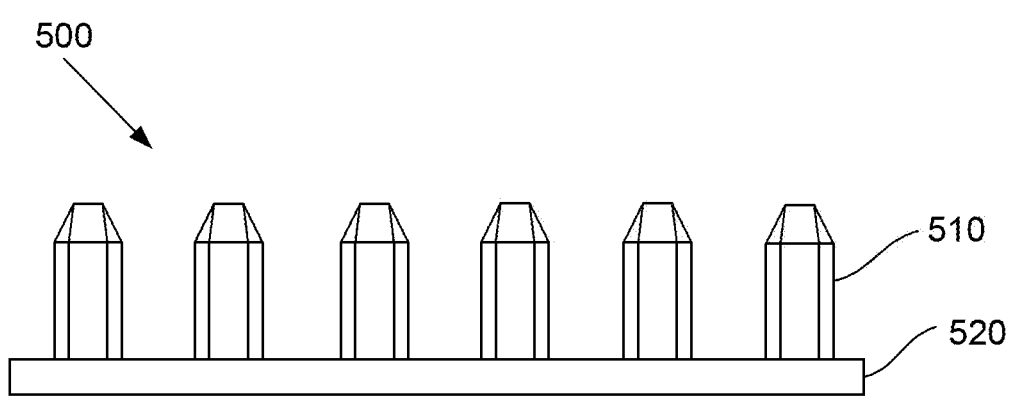
FIG. 5B is a schematic front view of a line of microprojections of the microprojection array.

An example of a microprojection array 500 is shown in FIGS. 5A-5B. The microprojection array 500 comprises a substrate 520 with a plurality of microprojections 510 protruding from the substrate 520. The microprojection array 500 includes microprojections 510 arranged in a number of straight, spaced apart lines as shown in FIG. 5B. In FIG. 5A, the spacing of the microprojections 510 between adjacent lines is indicated as $S_1$ and the spacing between successive microprojections 510 in the same line is indicated as $S_2$.

Figure 6C:
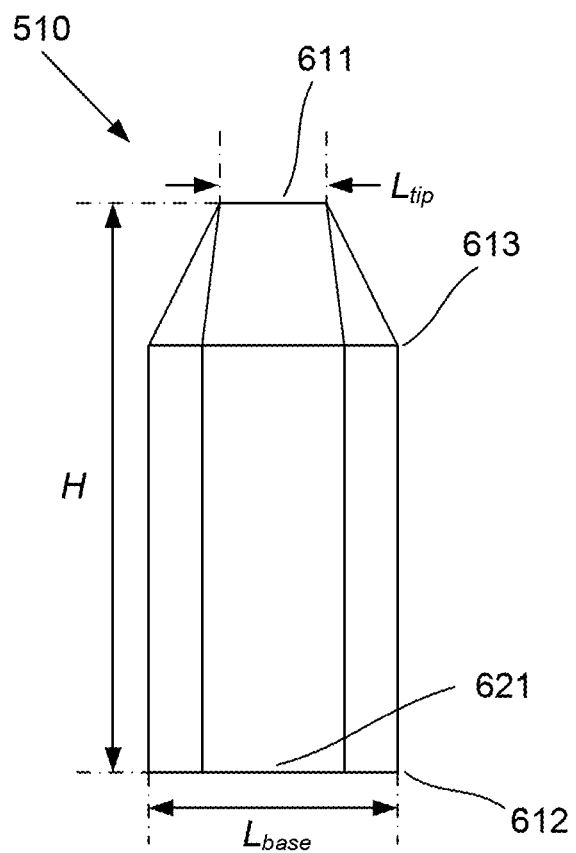
FIG. 6C is a schematic plan view of the microprojection.
Figure 6C:
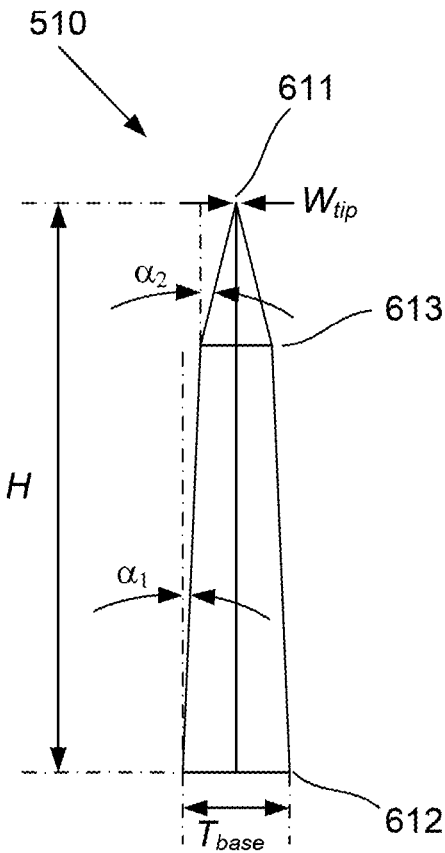
Figure 6C:
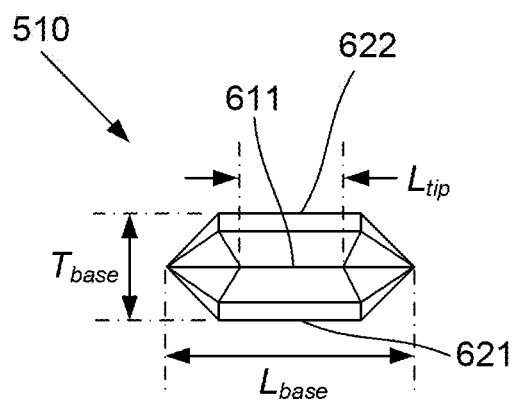

Further details of one of the microprojections 510 of the microprojection array 500 are shown in FIGS. 6A-6C. The microprojections 510 have a tapering hexagonal shape and comprise a tip 611 and a base 612 wherein the base 612 has two substantially parallel sides 621, 622 with a slight draught angle of approximately 1 to 20 degrees (as indicated in FIG. 6B by $\alpha_1$) up to a transition point 613 at which point the angle increases to from about 20 degrees to about 70 degrees (as indicated in FIG. 6B by $\alpha_2$). Although this example depicts a distinct increase in the angle at the transition point 613, it should be noted that there may be a more gradual increase in the angle than depicted. The tip 611 of each microprojection 510 terminates in an elongate edge. The tip 611 has a width $W_{tip}$ and a length $L_{tip}$. The base 612 has a length base, and is greater in length than the tip 611. The base 612 has a thickness $T_{base}$. The cross sectional length:thickness aspect ratio of the base 612 is defined as $L_{base}:T_{base}$, and is greater than 2:1 in this case. Each microprojection has an overall height H which depends upon the depth of penetration required.

In view of the above, it will be appreciated that the present invention relates to microarray projections which are designed to have a large surface area to frontal profile design while maintaining a high density configuration. The microprojection arrays of the present invention exploit the manner in which skin punctures. On a micro-scale, puncture is a function of crack formation in the skin and the subsequent growth of these cracks. While high density microneedles or microdevices perform this in a large number for every individual "needle", it necessitates a very large number of crack initiations thereby absorbing substantial energy. The devices of the present invention use a lower density of protrusions compared to some high density arrays, which have a line of contact rather than a single contact point. Once the crack in the skin starts to form, the protrusion will easily enter the skin, allowing internal skin surface area contact with penetrating surface. This means that significantly more surface area for the protrusion to enter the skin. The microprojections of the present invention may be wider and thinner than current conically or cylindrically shaped microprojections. Thus, a single line of contact may cut into the skin rather than point punctures. The results are that a larger surface may be introduced into the skin rather than individual points penetrating the skin in which each point must be opened before vaccine may be delivered.

The present invention relates to microprojection arrays where the microprojection design provides an alternative mode of skin puncture and vaccine delivery into the skin. The microprojections of the present invention are designed to have a large surface area to frontal profile design while maintaining a high density of microprojections on the array. The microprojection arrays of the present invention have a plurality of microprojections that are located upon a base. In one embodiment the microprojection have a shape that from a top down perspective is approximately an extended hexagon with two parallel sides being extended to give a rectangular profile with triangular ends. In an alternate embodiment the microprojections have a shape that from a top down perspective is approximately an extended octagon. This profile is similar to the hexagonally-shaped microprojection except that the ends of the microprojections are broadened. The microprojections may be aligned in parallel line with spacing between the edges of the microprojections. The microprojections may extend vertically to a length that will provide for drugs or vaccines to be delivered to the desired location within the skin.

The present invention relates to microprojections having a tapering extended hexagonal or octagonal shape comprising a base and a tip wherein the tip has a width of from about 0.5 μm to about 2 μm and a length of about 10 μm to about 2 mm.

The present invention relates to microprojection arrays comprising a plurality of microprojections wherein the microprojections have a tapering extended hexagonal shape or octagonal and comprise a base and a tip wherein the tip has a width of from about 0.5 μm to about 2 μm and a length of about 10 μm to about 2 mm.

The present invention relates to microprojection arrays comprising a plurality of microprojections organized in lines on the array wherein the microprojections have a tapering extended hexagonal or octagonal shape and wherein the spacing of the microprojection between adjacent lines is 100 μm and the spacing between successive microprojections is 80 μm. The present invention relates to methods of administering a vaccine to a human comprising applying the microprojection arrays in which vaccine is coated onto the microprojections of the arrays of the present invention to a human's skin.

The present invention relates to microprojection arrays comprising a substrate with a plurality of microprojections protruding from the substrate wherein the microprojections have a tapering hexagonal or octagonal shape and comprise a tip and a base wherein the base has two substantially parallel sides with a slight draught angle of approximately 1 to 20 degrees up to a transition point at which point the angle increases to from about 20 degrees to about 70 degrees.

The present invention relates to microprojection arrays where the substrate is solid or non-porous or non-hollow. The present invention relates to microprojection arrays where the microprojection array includes a number of microprojections arranged in a line. The present invention relates to microprojection arrays where the line is a straight line or a curved line or a circular line extending circumferentially around an axis. The present invention relates to microprojection arrays where some of microprojections in a line have a common base. The present invention relates to microprojection arrays where the microprojection array includes a number of spaced apart lines. The present invention relates to microprojection arrays where the spacing of the microprojections between adjacent lines is less than 200 μm or less than 150 μm or about 100 μm. The present invention relates to microprojection arrays where the spacing between successive microprojections is less than 200 μm or less than 150 μm or less than 100 μm or about 80 μm.

EXAMPLES

Example 1

Methods

All microprojection arrays were coated in a solution of 1% methylcellulose and the required vaccine dose dissolved in injectable phosphate buffered saline solution (Chen, et al, J. Controlled Release (2009) 139, 212). Fluvax 2014° was used as the antigen. Delivered dose was measured using radioassay (Fernando, et al. PLos One (2010) 5, e10266). Specific pathogen-free female C57BL/6 mice from 6 to 8 weeks old were used in all examples. Groups of 5 mice were use in each Example. Application of all microprojection array patches were performed as described (Crichton et al., Biomaterials (2010) 31, 4562) at a velocity of 2.3 m/s. The surface area and volume of the projections entering the skin was calculated upon models using Solid Edgex software (Siemens PLM Software, Texas, US). Imaging of microprojection array puncturing and delivery into the skin was performed by coating the microprojections with Fluorospheres (Molecular Probes, OR, US) and applying the microprojection arrays to skin for histology or excised skin for CryoSEM and imaging as described (3). Trans-Epidermal water loss (TEWL) was measured using a Tewawater® TM300 (Courage & Khazajka Electronic GmbH, Cologne, Germany). Mice had TEWL measurement taken prior to microprojection array application, immediately post-microprojection array application and at 30, 60, 90 and 120 minutes and then every hour from 3-8 hours post application of the microprojection array. Two control mice that had not had microprojection arrays used on them were also measure during these timeframes to observe any environmental baseline changes. Visible staining of the tissue and quantification of live/dead cells was performed as described (Depelsebaire et al., J. Invest. Dermatol. (2014) 134, 2361). A total of n=4-5 fields of view were acquired per sample. Skin infiltrating cells were examined by flow cytometry. Excised ear tissue was diced and incubated in 1 mg/ml collagenase IV (Life Technologies, Carlsbad, Calif.) and 4 U DNAse I (ThermoFisher Scientific, Pittsburgh, Pa.) for 30 minutes at 37° C. before inactivating with 200 uL of fetal bovine serum. Lysates were passed through a 70 μm strainer and cells pelleted by centrifugation with an additional 4U DNAse I treatment. Cells were incubated with purified anti-CD 16/32 (Clone 93, Biolegend, San Diego, Calif.) for 15 minutes at 4° C. before washing and staining with a cocktail of fluorescently conjugated anti-mouse monoclonal antibodies for 30 minutes at 4° C. CD45.2 PercP Cy5.5 (clone 104), CD11c PECy7 (N418), Ly6C APC (HK1.4RUO) (all from Affymetrix, San Diego, Calif.) CD11b Brilliant Violet 605 (M1/70), F4/80 Brilliant Vioet 421 (BM8) (Biolegend, San Diego, Calif.) and Ly6G FITC (IA8), Siglec F PE (E50-2440) (Becton Dickenson, Franklin lakes, NJ). Data were acquired on a BD LSR II flow cytometer and analysed using Flowjo v9 (TreeStar, Ashland, Oreg.). DRAQ 7 (Biostatus, Shepshed UK) was used to exclude dead cells before analysis. Doublets and debris were removed based on forward and side scatter properties before gating. Results were analysed using a one-way ANOVA with Tykey post-test in Graphpad Prism® Version 6.00. Ig titers were determined as described (Fernando, et al. J. Controlled Release (2102) 159, 215) except 5 ul of K-Blue TMB substrate (ELISA systems) was added and the color reaction was developed for 5 minutes in the dark. The reaction was stopped by the addition of 50 ul of 1M phosphoric acid and the plates were read spectrophotometrically at 450 nm.

Example 2

Coating and Skin Penetration of Microprojection Arrays

One embodiment of microprojections of the present invention (TP) and cylindrically/conically shaped microprojections (NP) were coated (Chen, et al, J. Controlled Release (2009) 139, 212) and the microprojection arrays were administered to mouse ear skin (Crichton, et al., Biomaterials (2010) 31, 4562). FIG. 1 shows the microprojections before coating. The coating solution is localized around the tips of the microprojections. Post-skin application imaging demonstrated that the coating on the tips of the microprojections had been removed and that the microprojections had entered the skin as evidenced by the tide mark on the microprojections' surfaces. Both TP and NP microprojections show varied penetration over the array surface indicating the complexity of penetrating a topographically variable skin surface. The TP microprojection shows a deeper penetration indicating the full dermis had been penetrated whereas the NP microprojections appear to have penetrated the epidermis and upper dermis. There appears to be a greater overall coverage of delivery by TP when an overhead view is surveyed.

Example 3

In Situ Effect of Microprojection Arrays Using CryoSEM

The mechanism of surface puncture was explored using CryoSEM which involved the freezing of skin with microprojections in place and then removing or fracturing the microprojection arrays and skin to show the state of the tissue in-situ. Clear puncture marks are created by both sets of microprojection arrays and the skin is entered without a large disruption of the adjacent tissue. When the microprojection arrays are withdrawn from the skin the holes in the skin quickly closed. In observing the TP microprojection array it was determined that the major axis of the hole created by the microprojections is 36 µm when the microprojection is in-situ. The hole shrinks by approximately 10 to 30% to 25 to 33 µm after withdrawal of the microprojection array. The minor axis shrinks to 5-10 µm after an initial width of 20 µm, a reduction of 50-75%. The data indicates much larger residual stress in opening a hole across the major axis as opposed to opening a hole along the major axis. This supports the concept that crack growth along the major axis of the microprojection will be the main driver of penetration which can serve to reduce residual stress concentrations along this axis. In contrast, cylindrical or circular holes made by microprojections where the major and minor axis are the same or similar will close from all direction with considerable residual stress from all side of the microprojection. This shape of microprojection provides no stress relief to assist the penetration process. Trans-Epidermal Water Loss was measured in skin penetrated by both TP and NP microprojections. The skin penetrated by NP microprojections healed more quickly that skin penetrated by TP microprojections consistent with view that large cracks are formed during TP microprojection penetration.

Example 4

Microprojection Arrays Depth Penetration Using Fluorescent Dye

Skin vaccine delivery depth was quantified by measuring the depth to which fluorescent dye coated onto the microprojections reached within the skin (Crichton, et al., Biomaterials (2010) 31, 4562). NP microprojections delivered to a depth of 39.9±16.4 µm (n=5 mouse ears; 337 total measurements) and TP microprojections delivered to a depth of 59.7±20.9 µm (n=4 mouse ears; 386 total measurements). The same amount of force was used to deliver the microprojections arrays to the skin. The TP microprojections were more successful in penetrating more deeply into the skin. A greater vaccine dose was delivered by the TP microprojections.

Example 5

Model for TP and NP Microprojection Arrays Penetration

To confirm increased penetration by TP projections a 3D model of both microprojections was constructed in Solid Edge®. The surface area and the volume of the TP and NP microprojection arrays were calculated and then scaled to account for all the microprojections on both arrays. The calculation indicated that for a single TP microprojection the volume entering the skin was 2-3 times that of an NP microprojection. Due to the large number of microprojections on the NP array, the overall volume of the microprojections in the skin summed over the entire array is similar between the NP and TP array for a given depth of penetration. The surface area of the two arrays is also similar. The increase penetration of the TP microprojections into the skin results from a greater ability to penetrate the skin rather than the disproportionate volume or surface area penetrating into the skin at comparable depths. The increase volume of the TP microprojections indicates easier entry into the skin which appears to be due to fewer penetrating microprojection into the skin and microprojections expanding punctures through the skin surface.

Example 6

Influenza Vaccine Administration with TP and NP Microprojection Arrays

Figure 3:
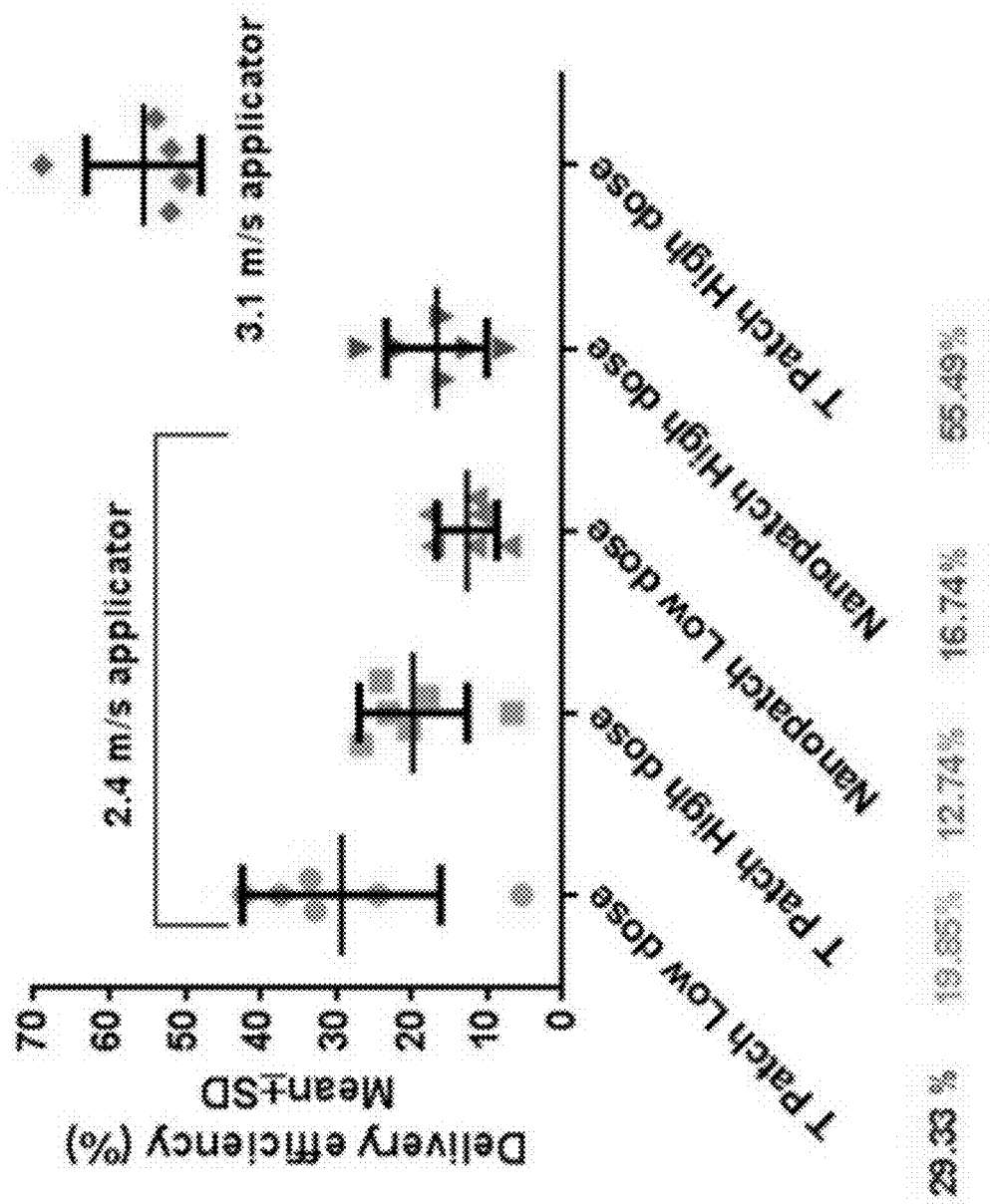
FIG. 3 is a plot of anti-Influenza antibody levels of sera from C57BL/6 mice determined by indirect ELISA plotted as 50% titers.
Figure 4:
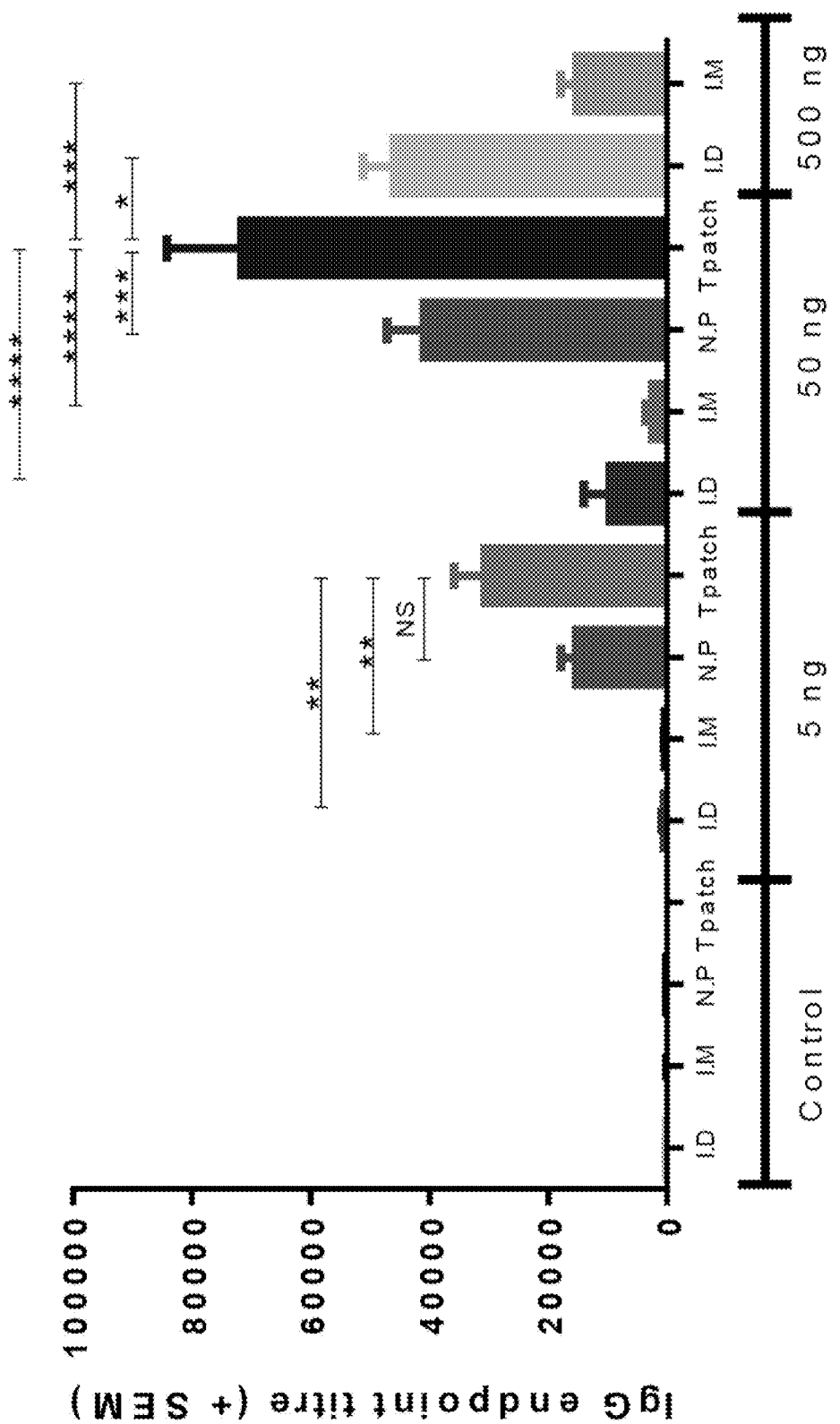
FIG. 4 is a plot of day 21 IgG Titers for 5 ng, 50 ng and 500 ng influenza doses administered intramuscularly, intradermally and by microprojection array TP and NP.

Five ng of commercial influenza vaccine (Fluvax®) was administered to pathogen-free female C57BL/6 mice from 6 to 8 weeks old using intradermal injection, administration of NP microprojection array, administration of NP microprojection array, or intramuscular injection. The results are shown in FIG. 3. The immune response to the TP microprojection array which held 5 ng of antigen was equivalent to the NP microprojection array response to 50 ng of antigen which indicates a 10 fold increase in immunogenicity by altering the shape and dimensions of the microprojections. The increased immunogenicity exhibited by the TP microprojection array is similar to the inclusion of a chemical adjuvant using the NP microprojection array. The use of TP microprojection array in delivering 50 ng of vaccine proved to a potent immune enhancer more than doubling the IgG titer of the elicited by the NP at the same dose (as shown in FIGS. 3 and 4).

Example 7

Cell Death with TP and NP Microprojection Arrays

Figure 2:
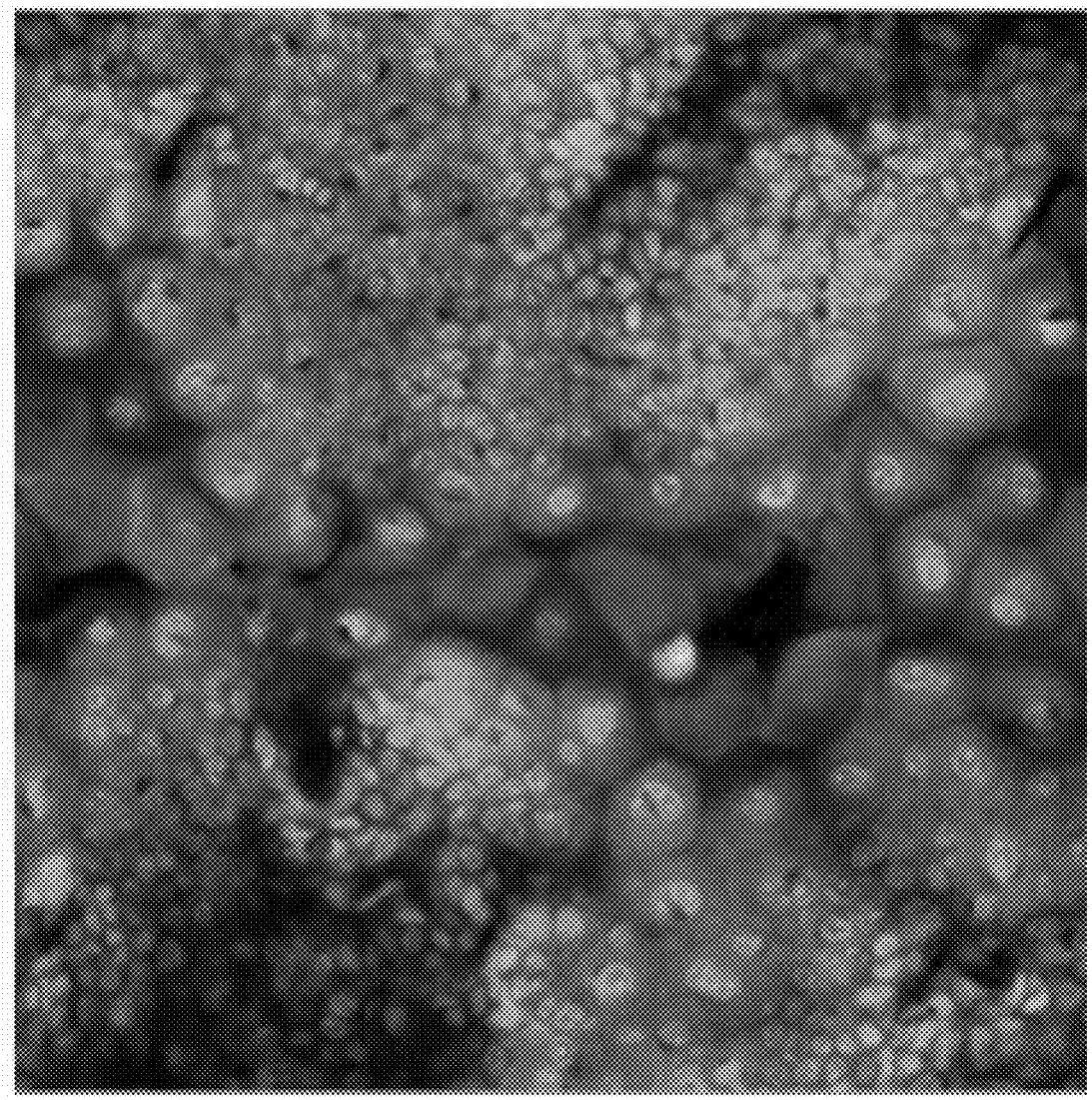
FIG. 2 is an image of skin stained to show live (green) and dead (magenta) cells following administration of one embodiment of microprojections of the present invention.

TP and NP microprojection arrays were applied to mouse ears and the skin stained for necrotic cell death and then imaged using confocal microscopy. An example of such an image is shown in FIG. 2. With respect to the NP microprojection arrays, cell death was observed within a radius of 20-30 µm with a greater number of dead cells on the edge of the array where bridged vaccine formulation restricted penetration but allowed significant force transmission into the skin. With respect to the TP microprojection arrays dead cells are observed primarily along the major axis of the microprojections. These extend approximately 5-25 µm from the centerline of the microprojections indicating that this area is the area of highest stress upon insertion of the array. On the edges of the array where there is higher stress and where there is some bridging of coating between microprojections the fractures of adjacent microprojections joined to form lines of continuous surface fracture, bordered by necrotic cells. This supports the idea that stress distribution and the crack growth makes it easier for TP microprojections to enter the skin. Quantifying the level of cell death around microprojection arrays revealed that TP in the central array area had 54.7±18.6 dead cells surrounding it and NP in the central array area had 21.8±3.0 dead cells surrounding it. On the edge of the arrays, the TP field of view there was 17.6% greater cell death than in the NP array. In the central area of the arrays, the TP field of view there was 42.7% greater cell death than in the NP array. The level of cell death results in an increased level of inflammation throughout the tissue which may be a stimulating factor for an enhanced immune response. The number of neutrophils and macrophages after administration of the TP array increased as opposed to the NP array. There also was a trend toward an increase in monocytes and eosinophils as well. The inflamed microenvironment may give an improved environment for dendritic cells to uptake vaccine and subsequently enhance immunogenicity.

Ranges may be expressed herein as from about one particular value, and/or to about another particular value. When such a range is expressed, another aspect includes from the one particular value and/or to the other particular value. Similarly, when values are expressed as approximations, by use of the antecedent about, it will be understood that the particular value forms another aspect. It will be further understood that the endpoints of each of the ranges are significant both in relation to the other endpoint, and independently of the other endpoint.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Within this disclosure, any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone", "only one," "not more than one", etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A method of administering a vaccine to a human comprising applying a microprojection array to skin of the human, wherein the microprojection array comprises a substrate with a plurality of microprojections protruding from the substrate wherein each of the plurality of microprojections have a tapering hexagonal shape and comprise a tip and a base wherein the base has two substantially parallel sides with a draught angle of approximately 0 to 10 degrees up to a transition point at which point the draught angle increases to approximately 20 degrees to 70 degrees and wherein the tip of each of the plurality of microprojections tapers to a distal line of approximately 25 µm long and 1-2 µm wide and wherein at least one of the plurality of microprojections is coated with a vaccine.

2. The method according to claim 1, wherein the plurality of microprojections include a number of microprojections arranged in a line, and wherein the method includes applying the microprojection array to the skin in a direction of movement including a component of movement aligned with the line.

3. The method according to claim 2, wherein the line is a straight line and the method includes applying the microprojection array to the skin in a direction perpendicular to the skin and laterally parallel to the skin in the direction of the line.

4. The method according to claim 2, wherein the line extends circumferentially around an axis and the method includes applying the microprojection array to the skin in a direction perpendicular to the skin whilst rotating the microprojection array around the axis.

5. The method of claim 1, wherein the microprojection array is administered to the skin by projecting the microprojection array into the skin at a speed of between about 20 m/s to about 40 m/s.

6. The method of claim 5, wherein a cell death response to the administration of the microprojection array is 50% greater than a cell death response to an administration of a microprojection array having conical microprojections administered at the same speed.

7. The method of claim 1, wherein an immunogenic response to the vaccine administered by the microprojection array is greater than an immunogenic response of the identical vaccine when administered by an intramuscular injection.

8. The method of claim 7, wherein the immunogenic response to the vaccine administered by the microprojection array is 50% greater than the immunogenic response of the identical vaccine when administered by the intramuscular injection.

9. The method of claim 7, wherein the immunogenic response to the vaccine administered by the microprojection array is 50% to 100% greater than the immunogenic response of the identical vaccine when administered by the intramuscular injection.

\* \* \* \* \*